US012440367B1

(12) United States Patent
Stock et al.

(10) Patent No.: US 12,440,367 B1
(45) Date of Patent: Oct. 14, 2025

(54) NASAL EPAP DILATOR

(71) Applicant: Stock IP Holdings LLC, St. Louis, MO (US)

(72) Inventors: Kevin J. Stock, Kirkwood, MO (US); Bradley L. Postier, St. Charles, MO (US)

(73) Assignee: STOCK IP HOLDINGS LLC, St. Louis, MO (US)

( * ) Notice: Subject to any disclaimer, the term of this patent is extended or adjusted under 35 U.S.C. 154(b) by 883 days.

(21) Appl. No.: 17/696,362

(22) Filed: Mar. 16, 2022

Related U.S. Application Data

(63) Continuation-in-part of application No. 16/558,286, filed on Sep. 2, 2019, now abandoned, which is a continuation-in-part of application No. 15/260,573, filed on Sep. 9, 2016, now Pat. No. 10,525,227.

(60) Provisional application No. 63/165,767, filed on Mar. 25, 2021, provisional application No. 62/216,365, filed on Sep. 10, 2015.

(51) Int. Cl.
*A61F 5/08* (2006.01)
*A61M 15/08* (2006.01)

(52) U.S. Cl.
CPC .............. *A61F 5/08* (2013.01); *A61M 15/08* (2013.01)

(58) Field of Classification Search
CPC . A61B 5/08; A61F 5/08; A61M 15/08; A61M 15/085; A61M 16/0666; A61M 16/0683; A61M 16/0688; A61M 16/0816; A61M 16/0825; A61M 16/0833; A61M 16/0841; A61M 16/20; A61M 16/208; A61M 2016/0021; A61M 2016/0036; A61M 2205/0238; A61M 2205/3306; A61M 2210/0618
See application file for complete search history.

(56) References Cited

U.S. PATENT DOCUMENTS

| | | | | | |
|---|---|---|---|---|---|
| 2,431,649 | A * | 11/1947 | Moats | A61M 15/0031 | 128/203.24 |
| 2009/0308398 | A1* | 12/2009 | Ferdinand | A61M 15/085 | 128/207.18 |
| 2015/0040907 | A1* | 2/2015 | Hakim | A63B 23/18 | 128/205.24 |

* cited by examiner

*Primary Examiner* — Annette Dixon
(74) *Attorney, Agent, or Firm* — Carmody MacDonald P.C.; Kevin C. Staed; Dennis Jm Donahue, III

(57) ABSTRACT

A nasal EPAP dilator is employed as an intranasal device which effect differing degrees of inhibition/easing for exhalation/inhalation. An outer housing functions as a pair of connected mirror image nasal dilators, and a differential-action valve mechanism modulates the airflow through the passages defined by the dilators, when inserted. The valve inhibits exhalation, while opening easily to inhalation which in combination with the dilating effect is thereby eased over the absence of the nasal dilator. A dial assembly having one or more exhalation apertures can be opened to varying degrees to adjust exhalation resistances and EPAP strengths without removal of the device or valve interchange. The housings can include protrusions and may also have lateral ends with a slot that holds a head strap.

20 Claims, 19 Drawing Sheets

NASAL EPAP DILATOR

CROSS-REFERENCE TO RELATED APPLICATIONS

This application claims priority from Provisional Patent App. Ser. No. 63/165,767 filed on Mar. 25, 2021 and is a continuation-in-part of U.S. patent application Ser. No. 16/558,286 filed on Sep. 2, 2019 which is a continuation-in-part of U.S. patent application Ser. No. 15/260,573 filed on Sep. 9, 2016 which issued as U.S. Pat. No. 10,525,227 on Jan. 7, 2020 and which claimed priority from Provisional Patent App. Ser. No. 62/216,365 filed on Sep. 10, 2015, all of which are hereby incorporated by reference.

STATEMENT REGARDING FEDERALLY SPONSORED RESEARCH

Not Applicable.

APPENDIX

Not Applicable.

BACKGROUND OF THE INVENTION

Field of the Invention

The present invention relates to nasal dilators, and more particularly to nasal dilators which reduce constriction in the nasal passageway to decrease resistance to inhalation airflow and contain a valve and dial to adjust resistance to exhalation airflow.

Related Art

A significant percentage of the population suffers from respiratory issues when sleeping, resulting in complications ranging from the mild, such as snoring, up to the major, such as sleep apnea which can become substantial enough to even contribute to a sufferer's early death. Highly effective treatments, such as continuous positive airway pressure (CPAP) are available, if the patient is compliant. Unfortunately, the devices and the difficulties involved in using them continuously have greatly reduced the efficacious employment of CPAP devices, with studies reporting that significant percentages of patients are non-adherent to treatment protocols. Clearly, effective treatment options which users find more readily usable are needed.

The term Sleep Disordered Breathing (SDB) is used to refer to a range of sleep breathing issues, such as snoring, upper airway resistance, obstructive sleep apnea (OSA). One frequent characteristic of these types of breathing-while-sleeping issues is that the internal air passages include at least some that are defined by softer mucous membranes and are subject to inhalation pressure induced narrowing as a result. While each individual varies, certain commonalities among higher risk groups have been identified and various therapies have been developed to address these commonalities. Due to the high rate of non-compliance with CPAP therapy, and frequent lack of comfort even among the compliant, alternative SDB treatments are often explored as a first treatment option. One treatment approach that has shown substantial benefit and is among the first therapy options tested is oral appliance therapy (OAT). The American Academy of Sleep Medicine (AASM) and the American Academy of Dental Sleep Medicine (AADSM) have issued guidelines for the use of oral appliances in the treatment of OSA.

There are substantial numbers and types of oral appliances available that effect OAT with a variety of approaches, due to the differences among individual users. While the degree of benefit from OAT can vary, and many are designed to be variable among differing degrees of effect, it has often enough been found that there can be a tradeoff between the degree of benefit gained and the level of comfort of the user. Since the user needs to relax and sleep through the night, the comfort level can be critical. There are differing clinical measures of OSA therapeutic effect, and on at least some occasions it has been found that when the oral device was setup with sufficient action to achieve the needed level of therapeutic effect, that the patient no longer had the comfort level needed for successful sleep. In addition, attempts to achieve greater therapeutic outcomes with OAT have shown to lead to higher risks of adverse side effects which include, and are not limited to, temporomandibular disorder (TMD), occlusal bite changes, tooth movement, headaches, and pain associated with the head and neck and other potentially long term ramifications.

It should be understood that these past, and the present invention, nasal therapies have uses beyond their combination with OAT's and that none of these uses are being disavowed for such uses. The use of a nasal therapy to "perfect", so to speak, the benefits achieved with OAT are of particular note herein and the discussion of them is also fully expository of the benefits, functions, and manners of construction/use of either the past, or the present invention's, form of nasal therapy. Most nasal therapy approaches generally attempt to use manipulation of airways and their exits/entrances to modify internal air passage pressures in manners intended to further treat SDB similar to some of the effects of CPAP devices. While much still needs to be learned, it has been generally agreed that using elevated internal air passage pressures, for at least a portion of the breathing cycle, can contribute at least partial relief for symptoms of SDB. Among the approaches to providing relatively more comfort that has been employed to raise internal air passage pressure are at least partial obstructions to exhalation. It has been found that there are still levels of improvement in wearing comfort that are desired, as well as more complex differential shaping of exhalation vs. inhalation air flow passage modifications and adjustable air flow passages.

There are a number of different designs for nasal therapy devices, but they do not have the beneficial features and functionality of the present invention. For example, U.S. Pat. No. 7,735,492 discloses a nasal Expiratory Positive Airway Pressure (EPAP) device with a housing and an airflow resistor. Although this device's housing can serve as a nasal dilator when no resistor is in the housing, the addition of the airflow resistor to the housing increases the resistance to inhalation airflow, and the airflow resistor increases the resistance to exhalation airflow even more than the inhalation airflow. The increase in resistance to inhalation airflow is due to the inherent stiffness of the airflow resistor that is necessary for the flap valve to provide even more resistance to the exhalation airflow and to avoid blowout of the valve during normal exhalation situations according to the design of the flap valve and housing in the '492 Patent, such as when the flap blows through its annular seat, because this design does not use any type of support structure extending across the interior space of the housing to support the flap valve.

The devices disclosed in U.S. Pat. No. 6,626,179 is for another nasal EPAP device. Similar to the '492 Patent's device, the flap valve restricting device in this invention does not have any type of support structure extending across the interior space of the housing. Therefore, the flexible flap valve embodiment must have sufficient strength that it is sufficiently supported by the annular seat so that it does not blowout during normal exhalation. The supports for the ball valve embodiment also do not extend across the interior space of the housing, and even if they did so, the ball valve necessarily causes a resistance to airflow during inhalation although its resistance can be less than the exhalation airflow resistance.

Another nasal EPAP device is disclosed by U.S. Pat. No. 9,326,885. Similar to the '492 Patent, the cannula body or housing of this device can provide a radial outward pressure so as to slightly increase the size of the nasal vestibule. However, as with the other previously known EPAP nasal devices, the diaphragm-type valve in this device restricts airflow during both inhalation and exhalation. Similar to the other previously known EPAP nasal devices, the resistance to airflow during the inspiratory phase is less than the resistance to airflow during the expiratory phase. In addition to the relative stiffness of the diaphragm valve, this device also has an anchoring stem and retaining prong on the inner end of the cannula body which extends into the housing's interior space and prevents the valve from fully opening during inhalation.

Some different types of nasal EPAP devices use stopping mechanisms to prevent blowout of flap valves. For example, U.S. Pat. Nos. 8,302,607 and 7,987,852 disclose the use of mesh or cross-bars which limit the extent to which valves can flex during exhalation and serve as a stop to blowouts. However, these devices are held in place at the exit plane of the nasal passageway by an adhesive rather than being inserted into the nasal passageway. Accordingly, these devices do not have housings that dilate the nasal passageway sufficiently to improve inhalation airflow.

Similar to EPAP devices, there are nostril plugs that are used to reduce functional articulatory disorder by suppressing the leaking of exhalation from a nose. As particularly disclosed in US Pat. App. Pub. No. 2009/0194100 by Minagi, nostril plugs can be inserted into the nostrils to substantially close the nostrils during exhalation while helping the patient feel little discomfort in use, including allowing for inhalation through the nose in a way that approximates their natural state. The nostril plugs are designed to be used when a person is awake because they are used to help a person clearly utter sounds when speaking so the Minagi '100 Application explains how the nostril plugs and their connecting bars are made to have little discomfort and to be inconspicuous. The Minagi '100 Application even explains how the small connecting bars can be brought into contact with the philtrum and the outer ends of the nostril plugs can be inserted past the peripheries of the nostrils into the interior of the nostrils so that a person who faces the user hardly recognizes the presence of the nostril plugs. The nostril plugs are not designed to dilate the nostrils over their natural state, i.e., their baseline uninflamed state, or otherwise provide for increased inhalation airflow through the nostrils over their natural state. To dilate the nostrils would result in more discomfort in use than what is taught and suggested by the Minagi '100 Application because dilation would require housings that are sized larger than the natural state of the nostrils whereas the Minagi '100 Application teaches housings that are sized to the natural state of the nostrils either by taking molds of the natural state of the nostrils to create the housings or by making the housings from a low-repulsive resilient foam that conforms to the shape of the nostril. Since the Minagi '100 Application teaches that its nostril plugs should minimize discomfort and be inconspicuous when they are in use when a person is awake, particular features of the nostril plugs that result in these aspects of the invention are critical to the invention's design. Since the Minagi '100 Application is not designed to dilate the nostrils from their natural state, the Minagi '100 Application discloses the use of scattering prevention walls mounted within the housings of the nostril plugs, and persons skilled in the art would recognize that these walls can cause a restriction that inhibit inhalation airflow which is the opposite intention when a nasal device is intended to dilate the nostril. For a nasal device that is to be inserted into the nostril as a dilator, the internal space of the device should be kept free from walls or any other structures that could impede the inhalation airflow so the nostril plugs in the Minagi '100 Application not only would be unsuitable for use as nasal dilators because they could actually restrict the inhalation airflow, the Minagi '100 Application also teaches away from modifications to its device that would transform it from a nostril plug to a nasal dilator.

Nostril plugs designed for reducing functional articulatory disorder according to the teaching of the Minagi '100 Application not only fails to teach or suggest housings that dilate nostrils in their natural state, it teaches away from the dilation of the nostrils from their natural state because this would cause more discomfort when a person is awake and trying to speak. Similarly, the low discomfort teaching of Minagi '100 Application teaches away from ridges or other protrusions on the outside of the housing that could help keep the housing in place within the nostril. Additionally, the Minagi '100 Application also teaches away from housings that extend outside of the nostril or that have flanges outside the nostrils because these flanges would not be inconspicuous and teaches away from a head strap that would hold housings in place within the nostrils when a person is sleeping because this would increase the discomfort and not be inconspicuous. Therefore, although some embodiments disclosed by the Minagi '100 Application may appear to have a similar shape to some of the nasal EPAP device embodiments of the present invention, the particular features and functionality of the nostril plugs disclosed by the Minagi '100 Application, particularly the features of the housing that would not dilate the natural state of the nostrils because they would increase discomfort for an awake person or that would make the housing less inconspicuous.

Although existing nasal EPAP dilators (NED) can come with a variety of exhalation resistances and EPAP strengths by having different sized exhalation ports corresponding to different valves, there is a desire to provide improved functionality in a device which not only dilates the nasal passageway sufficiently to improve inhalation airflow but also has adjustment means for exhalation airflow whereby a user can tailor a NED device to their desired therapeutic need as well as comfort without replacing the valve. Presently, prior art dilators and separate EPAP devices nor prior art nose plugs that are designed to be used when a person is awake have taught or suggested an adjustment means that can allow a user to control exhalation airflow while the device is in place. Accordingly, there remains a need for a nasal EPAP device that has a valve to restrict the exhalation airflow and a dial to adjust exhalation airflow resistance without removing the device altogether and interchanging parts while also improving the inhalation airflow by dilating the nasal passageway and freely allowing airflow to pass through the valve during inhalation for a net reduction in the restriction to airflow during inhalation as compared to breathing without the nasal device.

SUMMARY OF THE INVENTION

A housing of variable shape is inserted into a user's nasal passageway to create a dilation beyond the natural state, i.e., their baseline uninflamed state. A number of valves, preferably flaps, within the housing with closed and open configurations respectively restrict and permit airflow within the dilated nasal passageway. The housing or a separate structure also includes an annular rim, a number of spars, or a screen that are used to provide a valve stop for the flaps in the closed position. The housing can be connected to another housing through a bridge connection that can be integrally formed with the housings or may be detachable from the housings.

In other aspects of the invention, the housings have tubular sidewalls that define a channel in the interior space for the nasal airflow and enact the dilated state for the nasal passage by defining an internal nasal air passageway that is greater than that which occurs normally in the baseline state without the presence of the NED device in the nasal passage. Since the housing both expands the nasal passage and resists passageway constriction during inhalation, insertion of a NED device will expand the effective nasal airway passage available during inhalation, in comparison to inhalation without any device at all. Accordingly, insertion of the NED device expands the effective nasal airway passage available during inhalation, in comparison to inhalation without any device at all creating a net increase of airflow.

In another aspect of the invention, a dial assembly connects to the outer end of the housing and includes exhalation apertures that are opened and closed with a dial actuator to allow for the precise tailoring of exhalation resistance by covering the exhalation apertures to more or less degrees. The ability to vary EPAP strengths with the dial without having to take the device out or change valves is a beneficial feature of the present NED device. The dial can cover, to variable amounts, the size of the exhalation ports which allows for the precise tailoring of the exhalation resistance to the particular needs of a user.

In another aspect of the invention, the exterior surface of the housings that are inserted into the nostrils have external ridges or other protrusions to help keep the housing in place within the nostril when a person is asleep.

In yet another aspect of the invention, a head strap can hold the nasal EPAP device in place within the nostrils when a person is asleep.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings. The drawings constitute a part of this specification and include exemplary embodiments of the invention, which may be embodied in various forms. It is to be understood that in some instances, various aspects of the invention may be shown exaggerated or enlarged to facilitate an understanding of the invention; therefore the drawings are not necessarily to scale. In addition, in the embodiments depicted herein, like reference numerals in the various drawings refer to identical or near identical structural elements.

FIGS. 23A-22F illustrate views of another nasal dilator with the valves clamped between the frame and flanges of the housing where the frame fits over the flanges.

DETAILED DESCRIPTION OF THE PREFERRED EMBODIMENTS

Figure 1B:
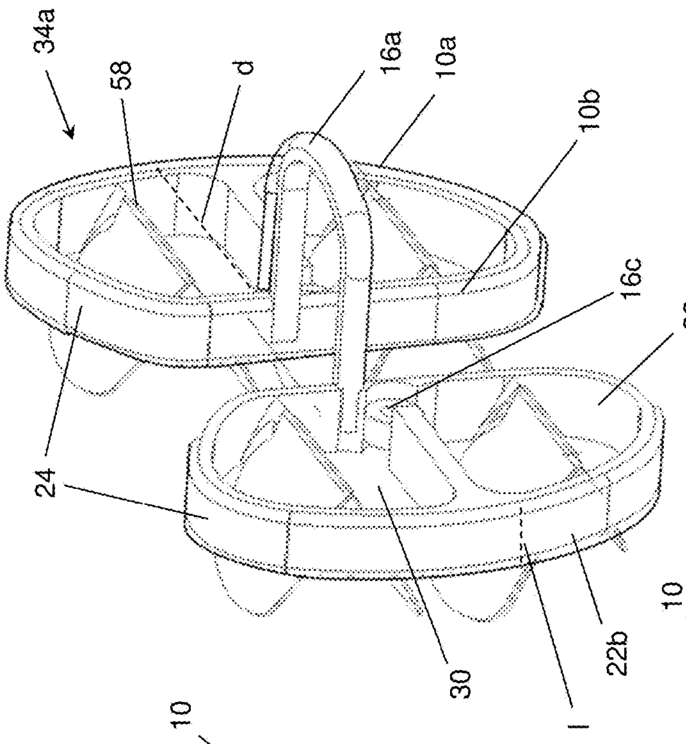
FIGS. 1A-1C are perspective and side views of a nasal dilator with flap valves in a planar frame housing.

The following description of the preferred embodiment(s) is merely exemplary in nature and is in no way intended to limit the invention, its application, or uses.

As generally shown in FIGS. 1-18 and 21-23, a nasal EPAP dilator (NED device) 100 has a housing 10, a seat 12 that is connected to the housing's opposing sidewalls 10*a*, 10*b* and spans the housing's interior space 30, and a valve 14 that is situated toward the inner side of the seat. The housing has an interior surface 22*a*, an exterior surface 22*b*, an inner end 22*c* and an outer end 22*d*. The seat is closer to the outer end of the housing than the valve, i.e. the seat is on the outer side of the valve, so that the seat provides support to the valve during exhalation and prevents a blowout of the valve during exhalation. The housing's 10 exterior surface 22*b* is shaped to fit within a user's nasal passageway and expands the nasal passageway to create a dilation 32 that is of sufficient strength to prevent the outer edges of nares from collapsing inwardly toward the nasal septum during inhalation, preventing or otherwise counteracting constriction during inhalation. During inhalation, the valve 14 is in its open configuration 34*a*, opening toward the housing's inner end, allowing air to flow freely through the dilated nasal passageway. During exhalation, the valve 14 is in its closed configuration 34*b* and is positioned against the seat 12. In the closed configuration, a back pressure is created while a small amount of air flows through the valve and out of the nasal passageway.

The shape of the housing 10 for the NED device 100 can vary to satisfy a range of shapes of nasal passages. According to the various embodiments described below, it will be appreciated that many different types of valves 14 can be used, such as a flap valve 46, a diaphragm valve 48, a hinged disc valve 50, an umbrella valve 52, and a duck valve 54. Additionally, according to the different embodiments, the seat 12 may be formed from spars 26, a screen 28, or any structural support that is connected to the housing's opposing sidewalls and spans the housing's interior space. For an oblong shaped housing, the spars 26 can be lateral spars 26*a* that span the shorter length of the interior space and/or longitudinal spars 26*b* that span the longer length of the interior space 30, such as shown in FIG. 13B. Preferably, the seat and valves are integrally formed with the housing, but they may also be formed separately and be connected by a mechanical means, such as a separate mount or an adhesive layer, or may be fused together, such as by heating.

The valve 14 is preferably formed from a flexible flap that may be integrally constructed with the housing 10 and spars 26 from the same flexible material. The flap membrane material can be sufficiently thin to readily curl, fold, or otherwise moved to open away from the seat during inhalation, whereas the thickness of the material for the housing and the spars are preferably sufficient to provide support for the dilation of the nasal passageway. In some cases, the valves 14 will be formed with predetermined resting configurations that incorporate curved topographies and/or ellipsoid cross-sections in order to facilitate one or more of opening the valves 14 during inhalation, and closing the valves 14 during exhalation. In addition to folding or bending, the operation of the flaps can also be enacted with hinged mounts; folding corrugations; apertures sliding on guidelines, rings, or wires; and other similar basic forms of pivoting interconnections. The materials used to form the NED device can be silicone, plastic, latex, or any other compound suitable for intranasal use and having the performance characteristics desired for freely flowing inhalation airflow and restricting exhalation airflow, and may be a thermoplastic material. For the valve membrane material in particular, silicone is the preferred material, and in addition to the other listed flexible materials, the use of some types of paper for the flexible valve is possible as well as other flexible materials.

Figure 19:
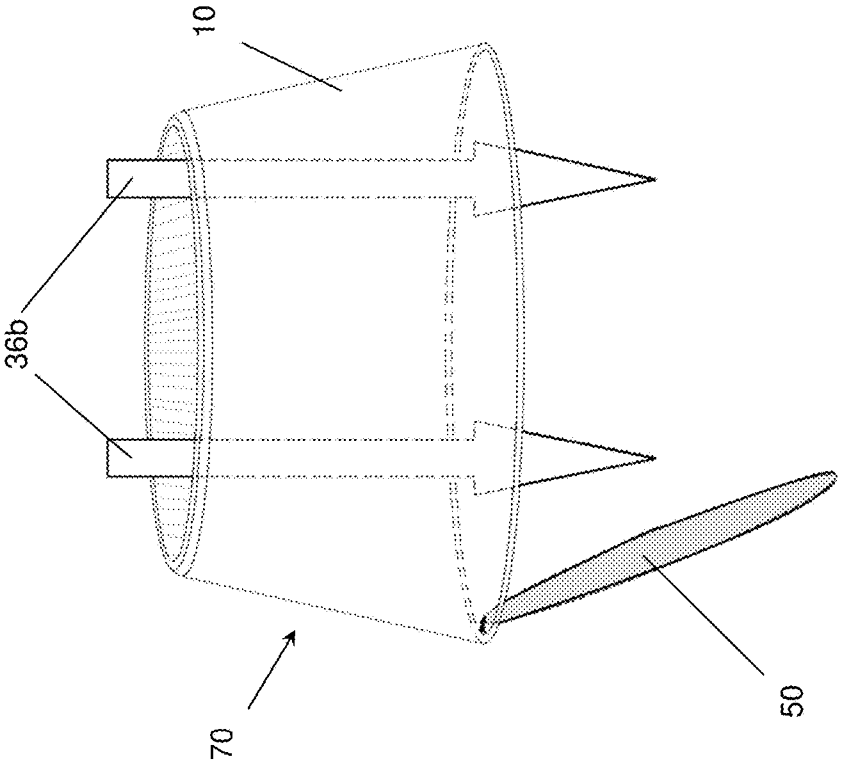
Fig. 19 PRIOR ART
FIG. 19 is a schematic view of a prior art EPAP device with a flap valve having an annular seat support but without a seat support spanning the housing interior space allowing the blowout of the flap valve.

Depending on the configuration of the valve 14 and the housing 10 and the connection between the valves and housing, the valve material may be formed from a more rigid material, such as substantially rigid plastic that may be connected by very flexible hinges. Again, the particular combination of materials for the valve, housing, and seat and their respective arrangements relative to each other should provide for freely flowing inhalation airflow and restricting exhalation airflow. With regard to the arrangement of the valve, housing, and seat, the seat 12 is connected to and situated toward the outer end of the housing to provide a stopping mechanism for the valve 14. The seat is on the outer side of the valve to prevent a blowout 70 of the valve 14 that is possible with the prior art, such as shown in FIG. 19 in which the valve is forced past the outer end of the nasal EPAP's housing. Accordingly, for the nasal EPAP dilator (NED) of the present invention, the seat allows the valve to be flexible enough so that it allows air to flow freely during inhalation and provides the support to the valve during exhalation to ensure that the valve provides the EPAP back pressure for the NED device 100. It will be appreciated that the spars 26 also provide structural support to the housing that helps with the dilation of the nasal cavity.

Generally, the NED device 100 will include two housings 10 to be used in both nasal passageways of a user. The housings 10 can be used by themselves or can be connected by one or more bridges that serve to maintain the orientation and pairing of the two housings 10. The bridge can also serve to help in the dilation of the nasal passages and may provide for convenience during manufacturing. The bridge also simplifies the usage of the NED device by providing a gripping portion that remains outside of the nose that helps in inserting the NED device into the nasal passageway and also helps in the removal of the NED device from the nasal passageway. A flexible bridge 16*a* that may be formed integrally with the housing and a more rigid, detachable bridge 16*b* may be formed separately from the housing and connected to the housing through bridge receivers 16*c* that are formed as a part of the housing. The bridge receivers 16*c* allow the rigid, detachable bridge 16*b* to be inserted and secured in a disposition roughly similar to that of the flexible bridge 16*a*.

Figure 2A:
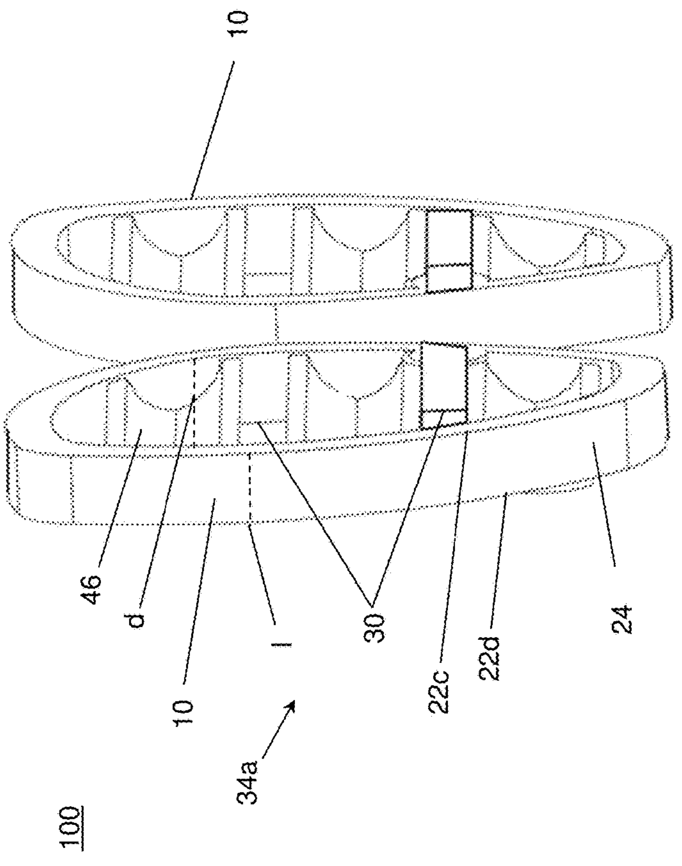
FIGS. 2A and 2B are a perspective and schematic view, respectively, of a nasal dilator with concave flap valves.

The housing 10 can be an elongated tube 22 or a planar frame 24. In the elongated tube 22 embodiments, the length (L) between the inner end of the housing and the outer end of the housing is longer than the distance (d) between the housing's opposing sidewalls 10*a*, 10*b* (L>d) as shown in FIG. 10A. In the planar frame 24 embodiments, the length (l) between the inner end of the housing and the outer end of the housing is either equivalent to or shorter than the distance (d) between the housing's opposing sidewalls 10*a*, 10*b* (l≤d) as shown in FIG. 2A. In the elongated tube 22 embodiments, the housing 10 can be either conical 78, such as shown in FIG. 11, or cylindrical 76, such as shown in FIG. 10A.

Figure 1A:
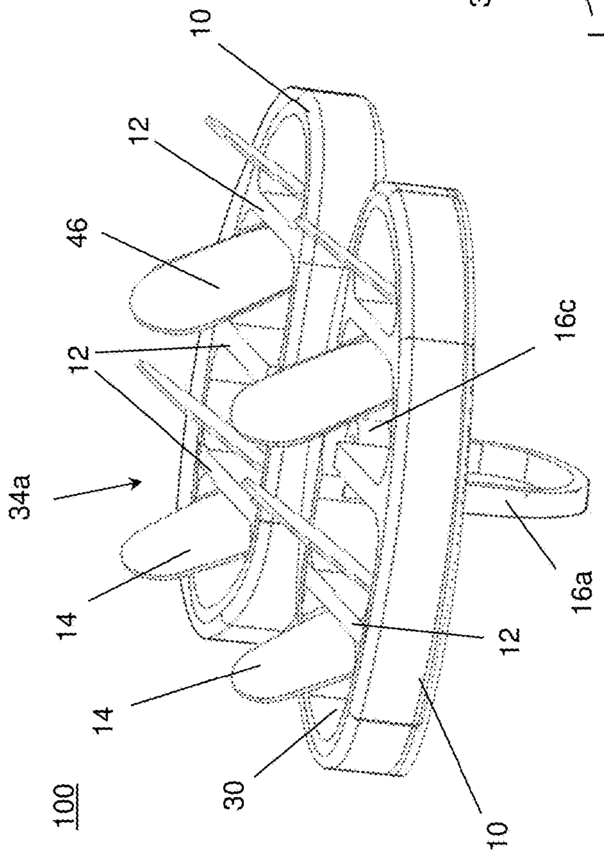
Figure 1C:
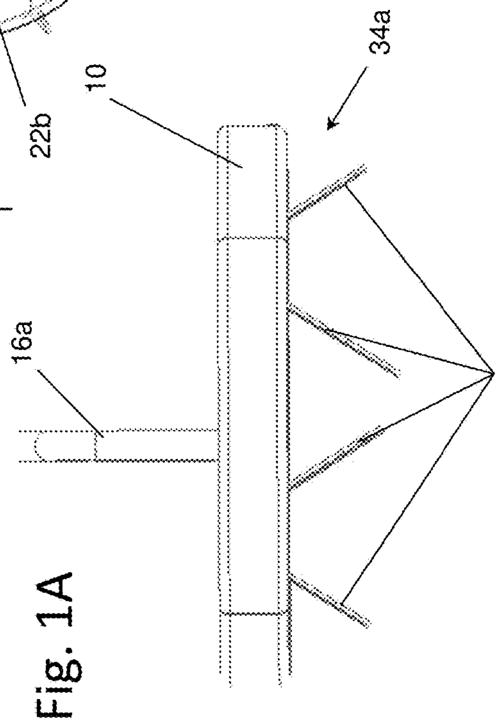

FIGS. 1A-1C depict an embodiment of the NED device 100 with flaps 80, 82 of the valve disposed in an open configuration 34*a* that will allow inhalation airflow 36*a* to pass through the interior space 30. In passing through the NED device, the inhalation airflow moves the flaps into a more open configuration 34*a*. The flaps meet at their wider ends at a juncture 58 which is interconnected with the housing 10. The juncture 58 can be constructed in a variety of ways, according to how the flaps are constructed, and the design objectives of a particular embodiment. In this first embodiment, the flaps are relatively stiff, so that the construction of the juncture 58 results in the free movement of the flaps. The juncture can be constructed as a hinging or folding articulation, or of a substantially flexible material such as silicone, among other variations. An instance of the first embodiment includes a pair of housings 10 which are generally not symmetrical, since they are designed to at least generally conform to the nasal passage's internal topography and to also dilate the nasal passageways beyond their natural state, i.e., dilation 32 of a constriction 210 in the baseline, uninflamed state of a nasal vestibule 220. A plurality of spars 26 extend across the shorter reaches of the housing 10 to span the housing's interior space. The spars also provide structural support to the housing 10 and prevent a blowout of the flaps so that the flaps are pressed against and stopped by the spars 26 during exhalation. While many of the embodiments of the present invention use a series of spars in each mirror image dilator, it is also within the scope of the present invention for a single spar to be used. Other embodiments show how the flaps may differ in size, shape, number, orientation, and manner of operation.

Figure 2B:
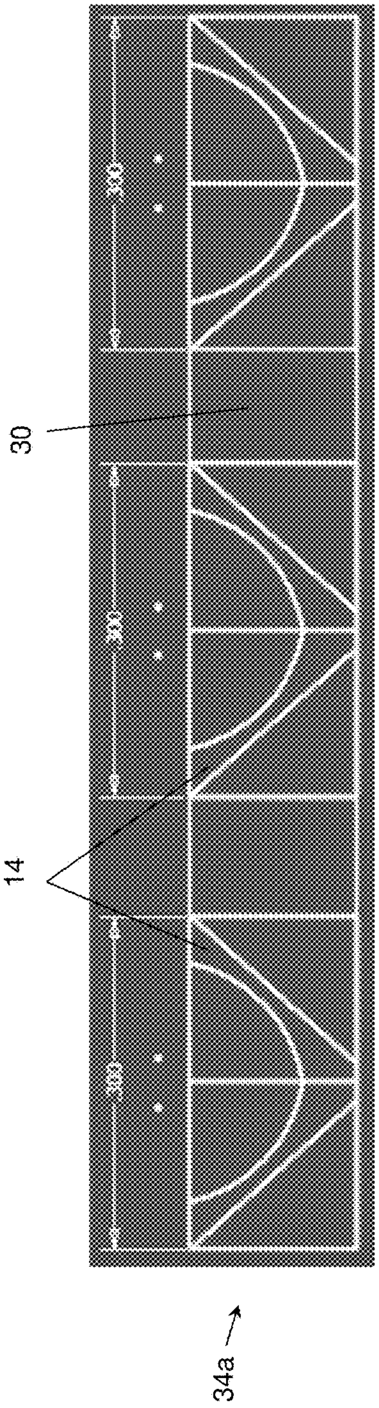
Figure 3A:
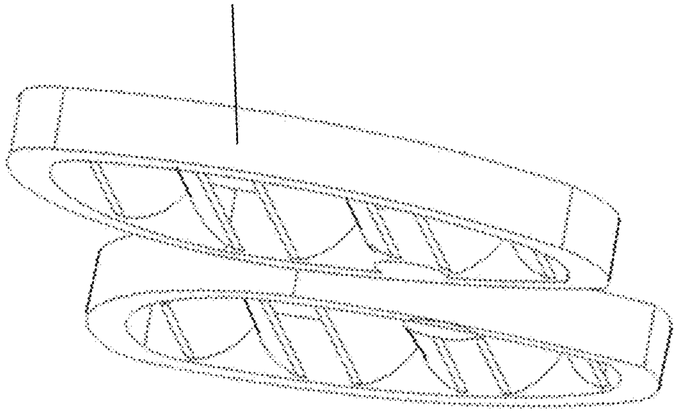
FIGS. 3A and 3B is a cross-sectional view and a schematic view, respectively, of a nasal dilator with convex flaps.
Figure 3B:
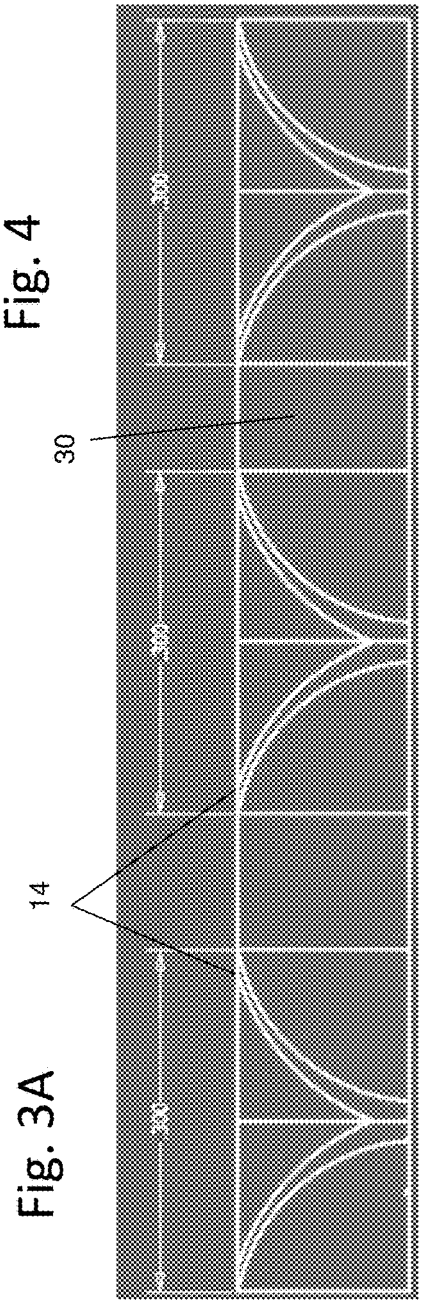

Further variations of other aspects of the present invention are depicted in the partial perspective schematic views of a concave flap cross-section embodiment, as shown in FIGS. 2A and 2B, and a convex flap cross-section embodiment, as shown in FIGS. 3A and 3B. In these two embodiments, the cross-section construction of the flaps 80, 82 is varied, both to manipulate the properties of the flaps' surfaces interactions with the airflow passing through the interior space 30 defined by the housing 10, as well as to manipulate how the flaps would bend or fold, when they are flexibly constructed. The convex flap embodiment depicted in FIGS. 3A and 3B is analogous to the concave flap cross-section embodiment in FIGS. 2A and 2B, with the variation that a plurality of flap faces are convexly configured, meeting in pairs at crossing lines.

Figure 4:
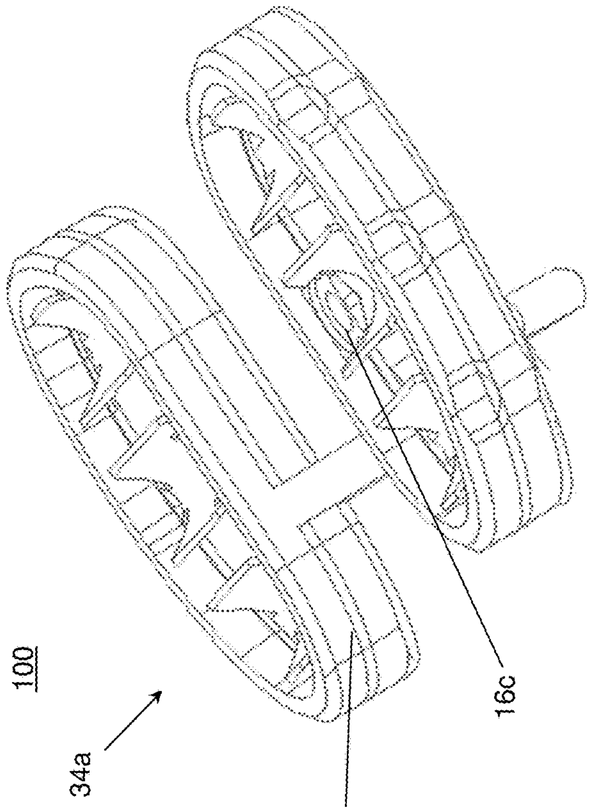
FIG. 4 is a perspective view of a nasal dilator with curved flap valves.

FIG. 4 illustrates a variation of the NED device 100 with curled flaps 80, 82. The curled flaps are constructed of a relatively steady thickness, preferably as thin as is effective, since the curled flaps are designed to operate the differential effect of assisting inhalation airflow 36*a* while blocking exhalation airflow 36*b* by flexibly deforming in response to the air flow. The side of the housing 10 shown directed upward in FIG. 4 in use is disposed within the nasal passage facing inward, in the direction of inhalation airflow 36*a*. The outer portions of the curled flaps increase in curvature when deformed by the inhalation airflow 36*a* thereby further opening the airflow passages, and are flattened and deformed by their curved topography catching the exhalation airflow 36*b* so that their outer portions will come to a closed configuration 34*b*.

Figure 5B:
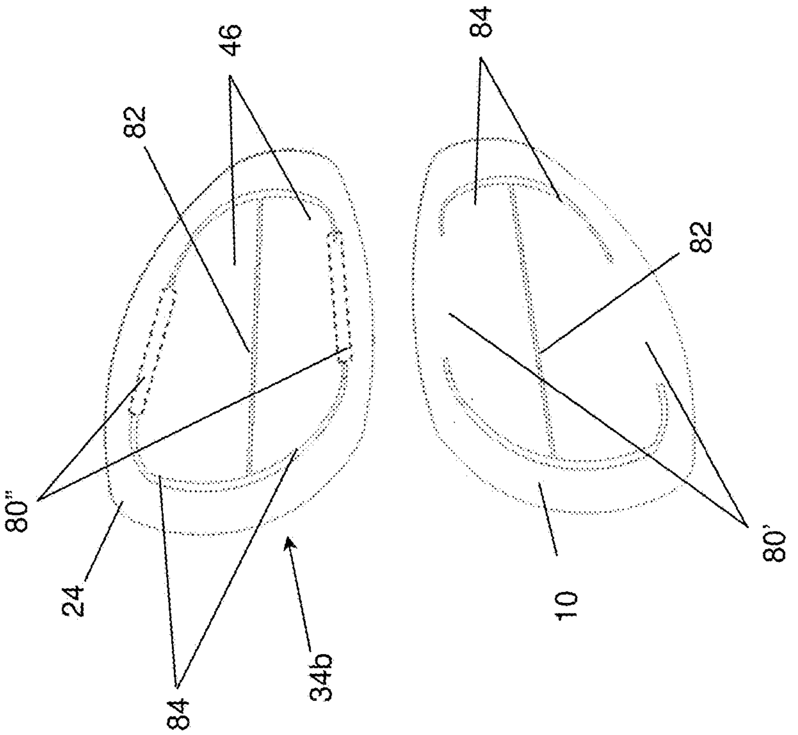
FIGS. 5A and 5B are bottom and top perspective views, respectively, of a nasal dilator with bi-flap valves.
Figure 5A:
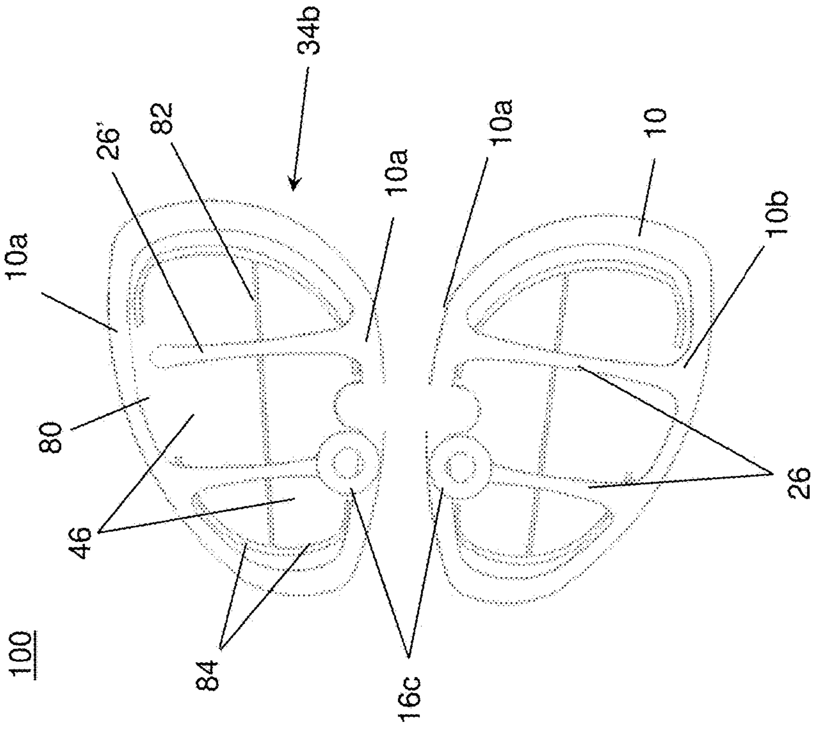
Figure 6A:
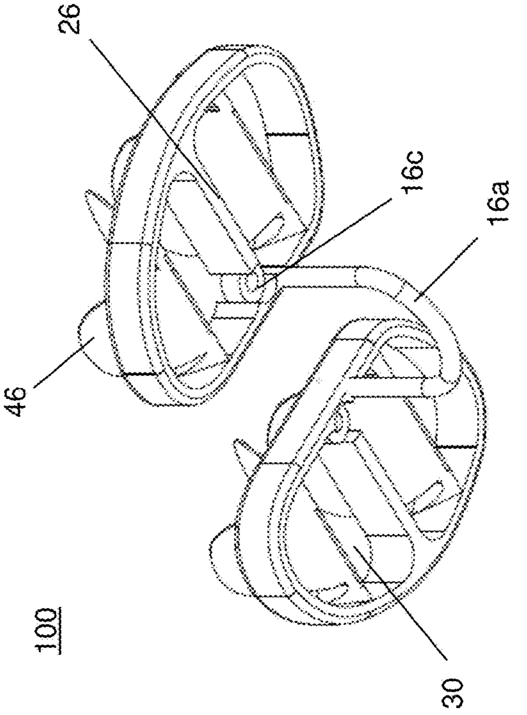
FIGS. 6A and 6B are bottom and top perspective views, respectively, of a nasal dilator with flap valves.
Figure 6B:
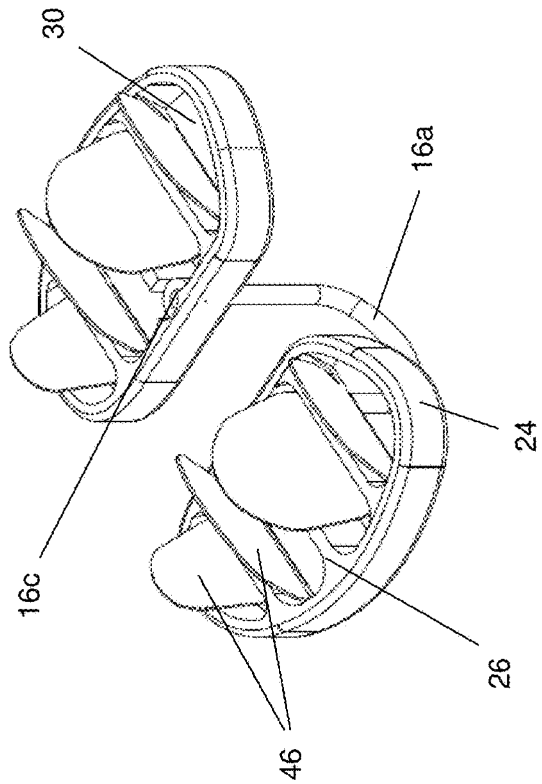

A bottom view and top view of the bi-flap embodiment, in a closed configuration 34*b*, are shown in FIGS. 5A and 5B, respectively. Generally, the flap valves have a fixed end 80 that are connected to the housing's sidewalls; according to the general description of the valves above, the fixed end may have an integrally formed portion 80' with either the housing or the seat or the valve may be formed separately and may have a mounting portion 80" that is connected to either the housing or the seat by a mechanical means, such as with a separate fastener or an adhesive layer or by a clamped engagement between the seat and the housing, or may be heat welded together. The flaps of the flap valves 46 can move freely at a free end 82 by a pair of sides 84 that extend from the fixed end to the free end. Preferably, the sides of the flaps have a curvature conforming to the shape of the interior surface of the housing. Alternative bi-flap embodiments are not shown, but are similar to the longer bi-flap embodiment, differing primarily by variations in the orientations of the flaps and spars 26. FIG. 5A also shows an example of a partial spar 26' that is connected to the housing 10 only at one end and extends across the interior space to prevent the blowout of the valve. Partial spanning spars or screens can provide more flex to the housing that may provide additional comfort and fit in the nasal passageway. Additionally, partial spanning spars or screens can have other potential benefits, including but not limited to, manufacturing, function, and customizability to nasal passageways.

Figure 7A:
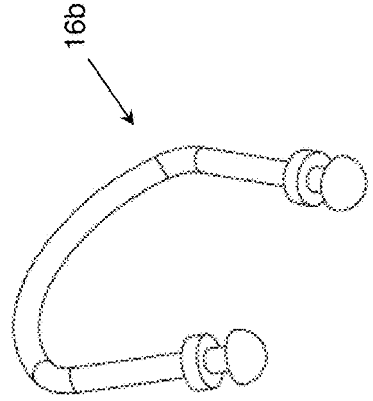
FIGS. 7A and 7B are a perspective view and a side view, respectively, of the detachable bridge.
Figure 7B:
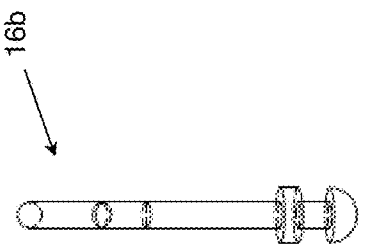

The detachable rigid bridge 16*b* is depicted in a perspective view in FIG. 7A and in a side view in FIG. 7B. The rigid bridge 16*b* is often constructed separately from the rest of the NED device 100, and hence is shown separately, but it should be understood that in use, the detachable bridge 16*b* will usually be fully integrated with the rest of the nasal EPAP dilator 100 by being inserted in the receiver 16*c*. The bridge is generally flat in profile, with a curved center region and straighter end regions. The bridge can be stretched and narrowed to configure to differing widths of nasal passages and adjusted to optimize fit as well as aiding in the stabilization of the housing and dilation of the nasal passages.

Figure 8B:
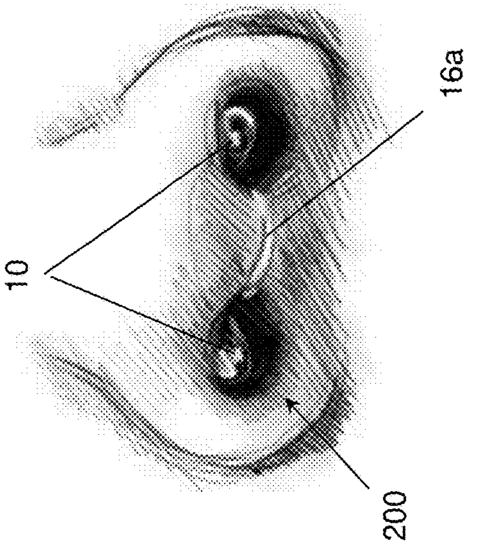
FIGS. 8A-8C are perspective, front and side views of the nasal dilator inserted within a user's nasal passageway.
Figure 8C:
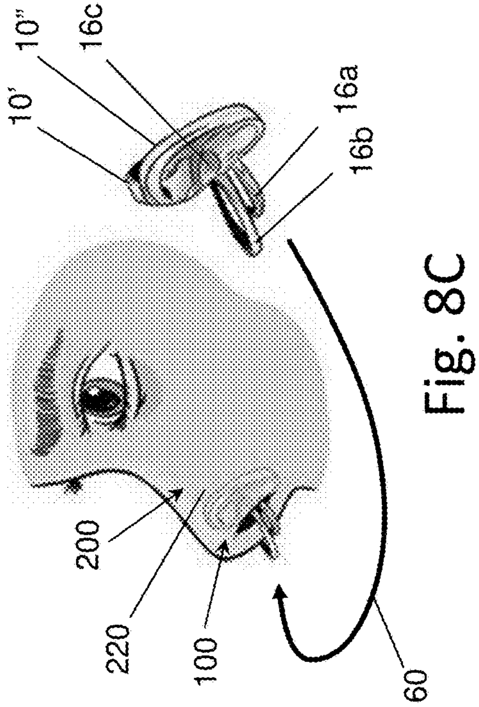
Figure 8A:
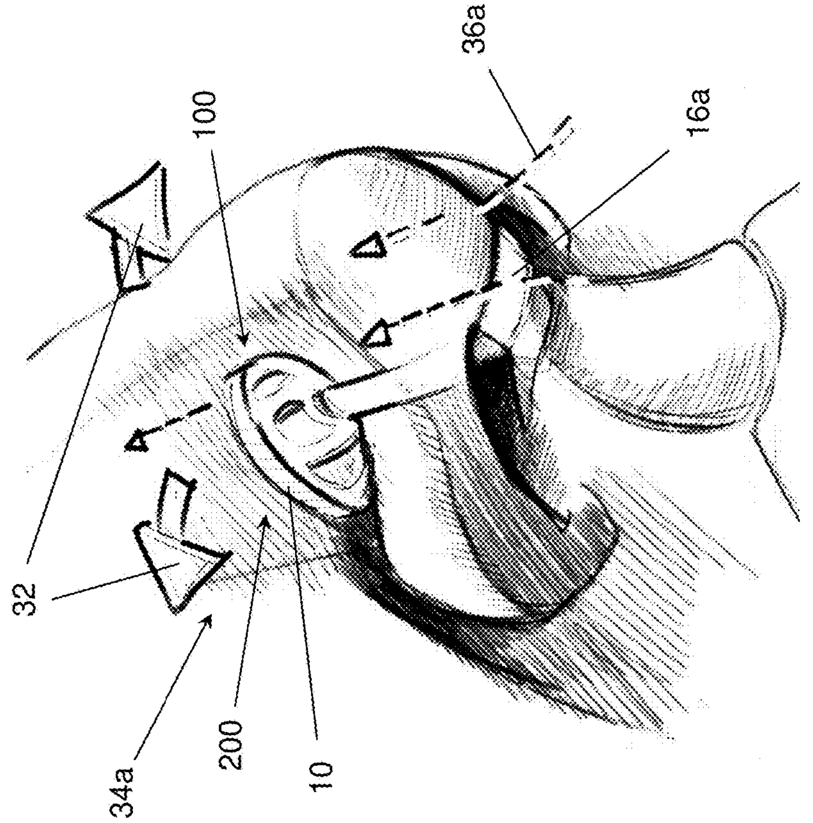

FIG. 8A illustrates a perspective view of the planar frame NED device 100 as it is installed to produce the dilation 32 of the nasal passageway 200. FIG. 8B is a front view of the NED device as it is installed with the bridge 16*a* between the housings 10. FIG. 8C illustrates the insertion 60 of a NED device 100; in this particular view, the planar frame NED device has a flexible bridge 16*a* that is integrally formed with the pair of housings 10', 10" and a more rigid bridge 16*b* that connected to the housings through the receiver 16*c* in each of the housings.

Figure 9B:
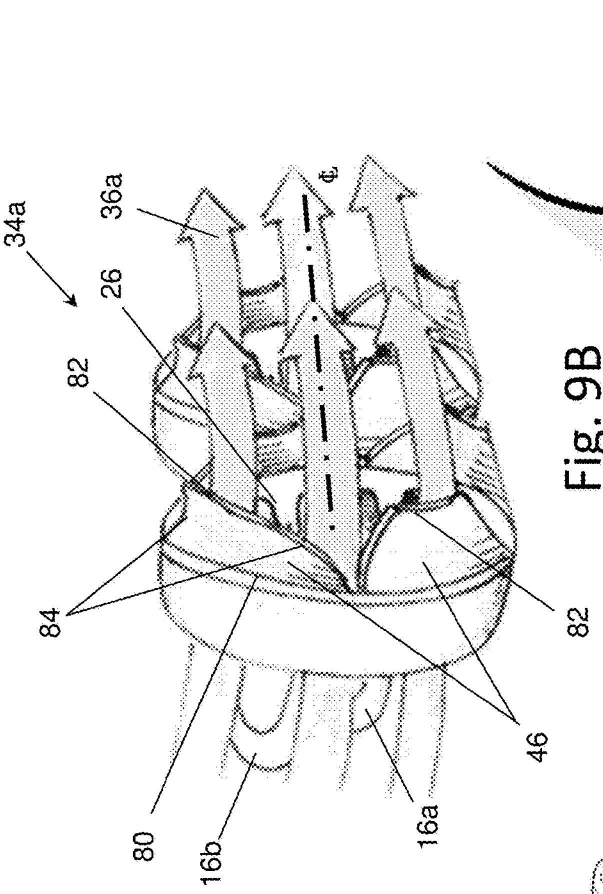
FIGS. 9A and 9B are schematic depictions of the nasal dilator with a multi-flap valve during exhalation and inhalation, respectively.
Figure 9A:
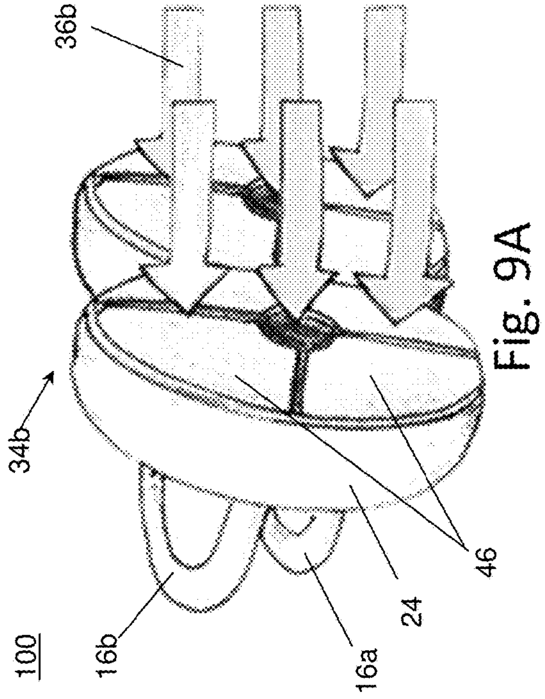

FIGS. 9A and 9B illustrate the airflow through the NED device 100 during inhalation and exhalation. During inhalation, the inhalation airflow 36*a* causes the valve 14 in the NED device 100 to operate in its open configuration 34*a* away from the seat 12. In this particular embodiment, the airflow forces the free end 82 of the flaps off of and away from the spars 26. The dilation produced by the housing during inhalation results in an increased airflow as opposed to airflow without the use of the NED device. FIG. 9A shows the exhalation airflow 36*b* during exhalation with the valve 14 in its closed configuration 34*b* forced onto the seat 12. The airflow pushes the flaps onto their respective spars 26 and the housing provides a seal with the nasal passageway around the periphery of its exterior surface, thereby decreasing the amount of air allowed through the NED device and out of the nasal passageway and providing a backpressure in the nasal cavity and airway.

For valves which use flexible flaps 80, 82, such as in the embodiment illustrated in FIGS. 9A and 9B and alternative embodiments described in detail below, the flexibility of the flaps is sufficient that when the inhalation airflow pushes the flaps open, the sides 84 curve toward the inner end of the housing 10 from their fixed end 80 to the free end 82. The housing has a central longitudinal axis, i.e., a centerline axis (℄), between its inner end and its outer end, and the flaps preferably have sufficient flexibility that the free end is aligned with or nearly aligned with the axis when the flaps are pushed open by the inhalation airflow.

Figure 10B:
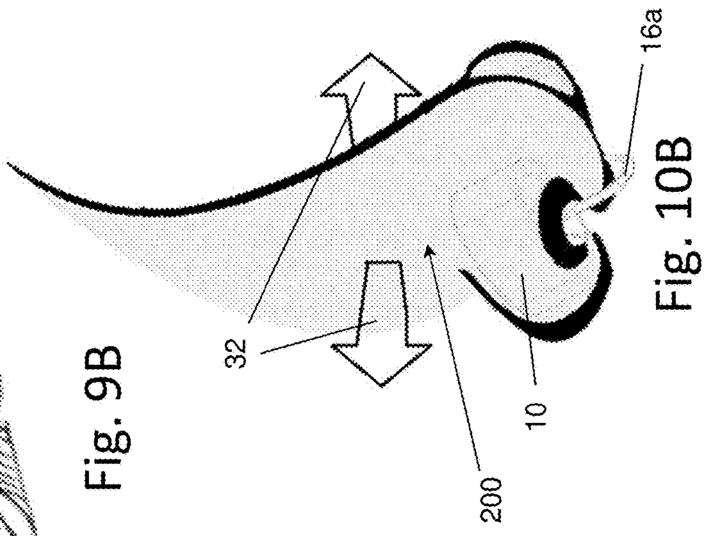
FIGS. 10A and 10B are perspective views of the nasal dilator with an elongated housing before installation and while inserted within a user's nasal passageway, respectively.
Figure 10A:
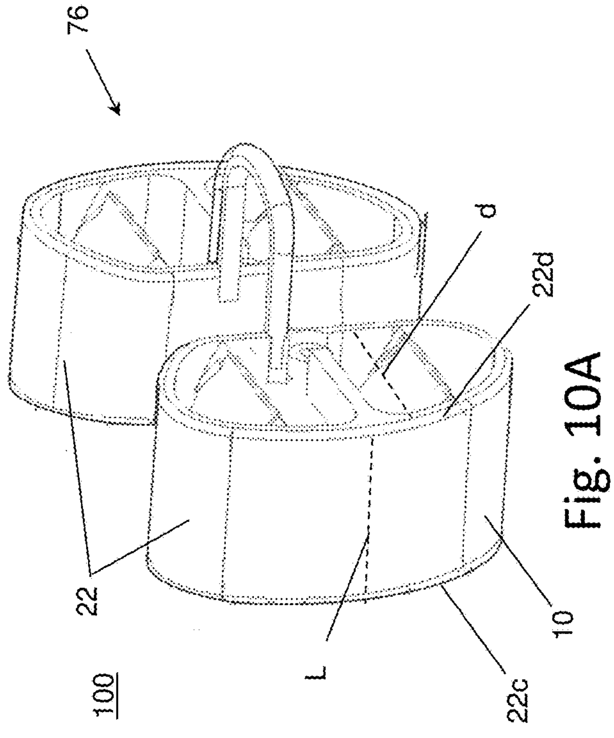
Figure 12:
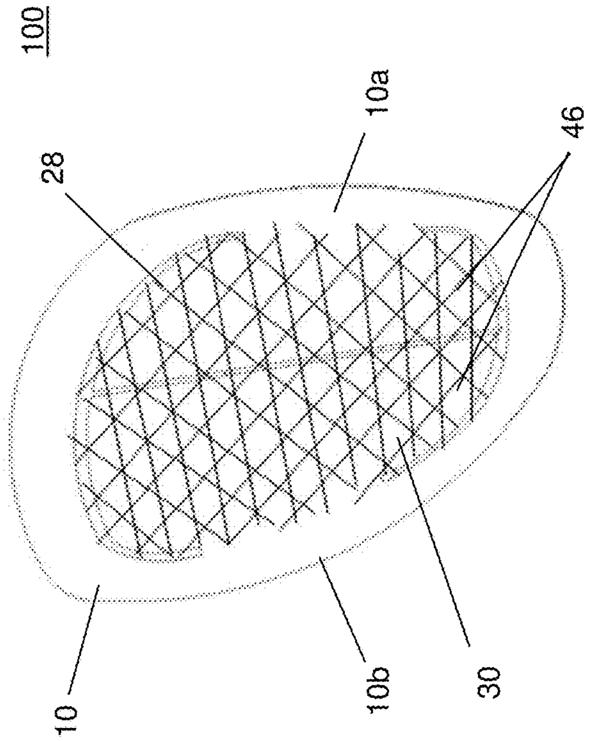
FIG. 12 illustrates the nasal dilator with a screen supporting the flap valves.
Figure 11:
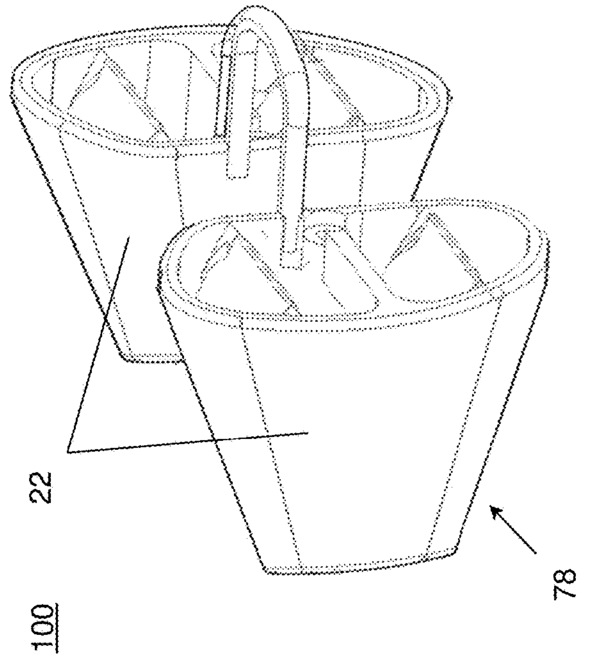
FIG. 11 illustrates the nasal dilator with a cone shape housing.

FIGS. 10A, 10B, and 11 show the NED device 100 in an alternative configuration in which the housing is an elongated tube 22. The tube shape in FIG. 10A is uniform in size of the interior space throughout, while the embodiment shown in FIG. 11 is more of a cone shape. FIG. 10B also shows how the device creates a dilation 32 of the nasal passage when in use. As shown in FIGS. 10 and 11, the seat can be formed from spars 26. Similarly, the seat can be formed from a screen 28 as shown in FIG. 12.

Figure 13A:
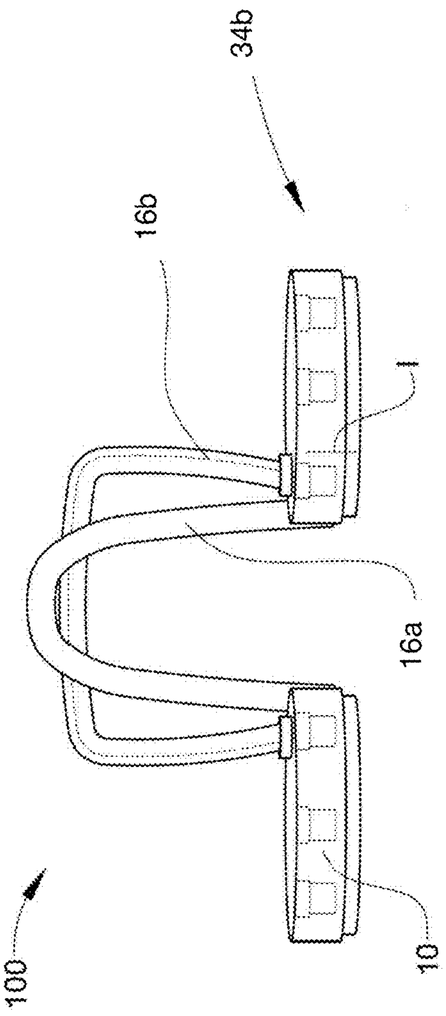
FIGS. 13A and 13B illustrate a side view and a bottom view, respectively, of the nasal dilator with a longitudinal spar intersecting with the lateral spars.
Figure 13B:
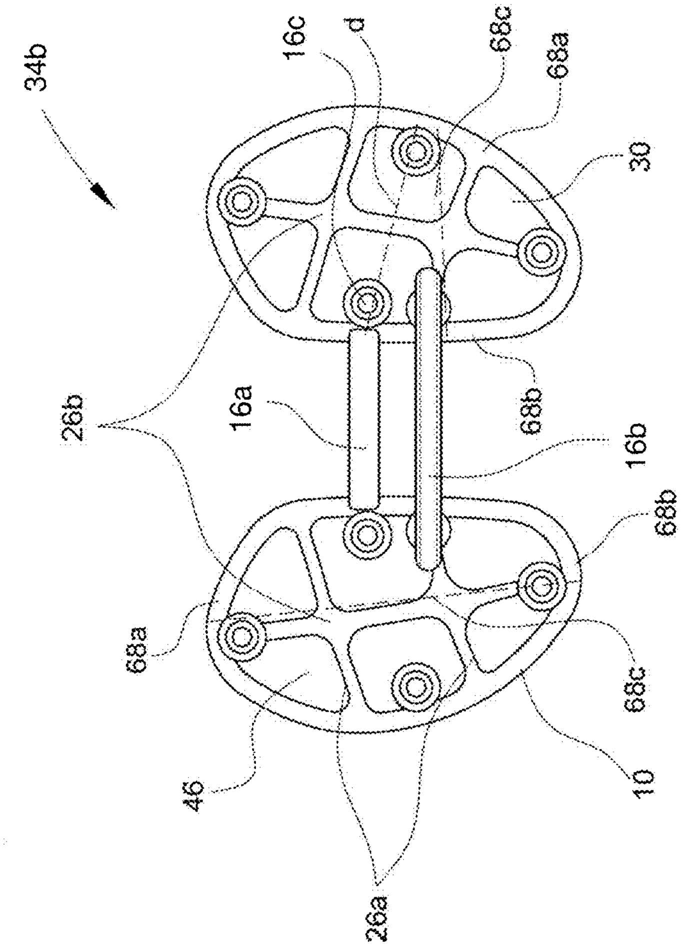
Figure 14A:
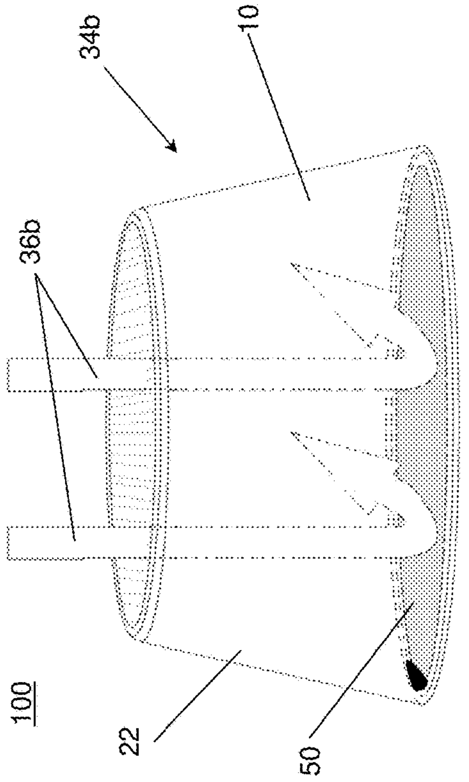
FIGS. 14A and 14B are schematic views of a nasal dilator with a hinged disc valve and screen during exhalation and inhalation, respectively.
Figure 14B:
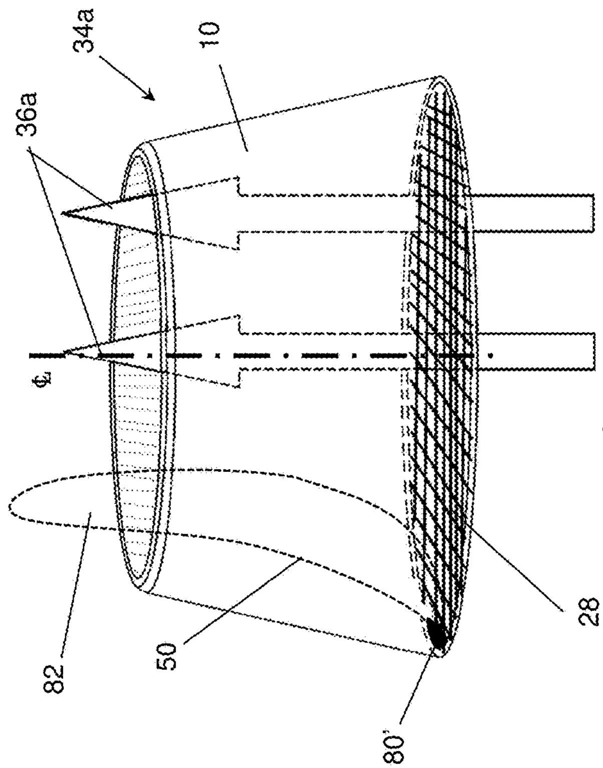

The embodiment of the NED device shown in FIGS. 13A and 13B has a seat that includes both lateral spars 26*a* and longitudinal spars 26*b*. The longitudinal spars intersect with the lateral spars providing further support for the housing 10 and the valves 14. This particular embodiment uses flaps 80, 82 for the valves. The lateral spars 26*a* span across the shorter distance 66*c* between lateral opposing walls 66*a*, 66*b* of the housing 10, whereas the longitudinal spars 26*b* span between the longitudinal opposing walls 68*a*, 68*b* at the longer distance 68*c*. It will also be appreciated that diagonal spars could be used such that they span the interior space of the housing similar to the screen shown in FIG. 12.

FIGS. 14-18 illustrate alternative embodiments of the NED device 100 using a variety of valves 14. FIGS. 14A and 14B display an embodiment using a hinged disc valve 50. In the closed configuration 34*b*, the hinged-disc valve 50 restricts the exhalation airflow 36*b* during exhalation creating a backpressure. The hinged disc valve 50 is prevented from the blowout condition by the screen 28, which is visible in the open configuration 34*a* shown in FIG. 14B. FIG. 14B also shows that the hinged disc valve 50 can bend and conform to the interior of the housing 10 to allow the inhalation airflow to freely pass through the interior space of the housing.

Figure 15A:
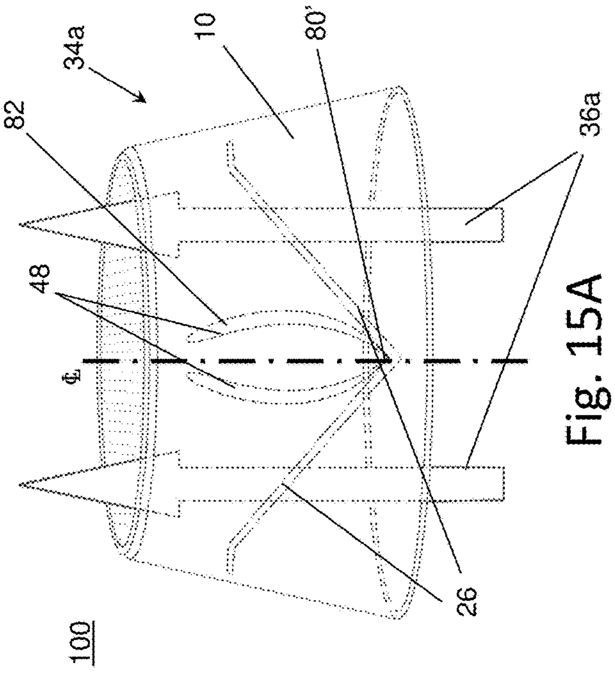
FIGS. 15A and 15B are schematic views of a nasal dilator with a diaphragm valve and angled spars during exhalation and inhalation, respectively.
Figure 15B:
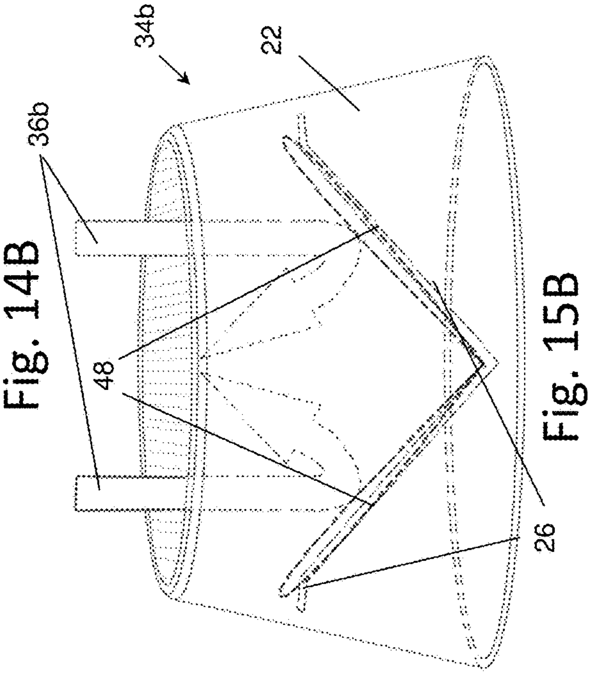
Figure 18:
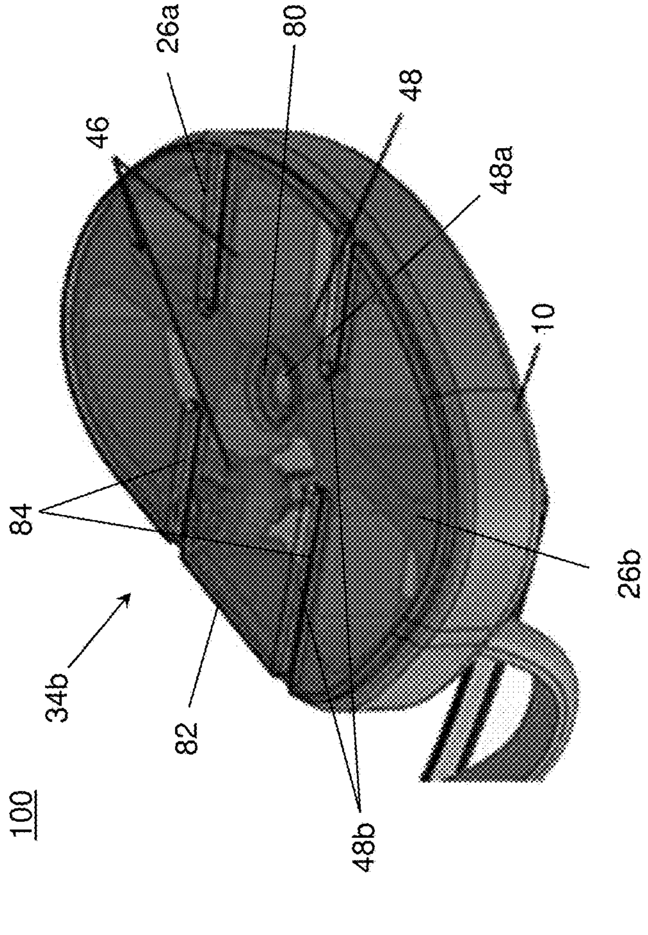
FIG. 18 is a perspective view of a nasal dilator with a diaphragm valve having slits and seated on longitudinal and lateral spars.

An embodiment of the NED device which uses different types of a diaphragm valve 48 is shown in FIGS. 15A and 15B and FIG. 18. FIGS. 15A and 15B shows the housing 10 as an elongated tube 22, and the seat 12 is formed by angled spars 26. In the closed configuration 34*b*, the diaphragm valve 48 expands and is pushed against the angled spars 26 by the exhalation airflow to create the backpressure. In the open configuration 34*a*, the flaps 80, 82 of the diaphragm valve 48 are nearly aligned with the housing's centerline axis (℄) which allows the inhalation airflow to freely pass through the interior space of the housing. FIG. 18 is a planar frame 24 version of the NED device with a diaphragm valve 48 that has a central mount 48*a* and slits 48*b*. The slits provide additional flexibility to promote inhalation airflow. In this embodiment, the seat is formed by intersecting lateral spars 26*a* and longitudinal spars 26*b*. The central mount can be a separate structure with a mechanical connection to the seat or it can be integrally formed with the seat or it may be otherwise adhered or fused to the seat.

Regardless of the connection formed by the mount between the valve and either the seat or the housing, the mount is on the outer side of the valve, preferably connected directly to the seat, and no part of the mount nor any anchoring stem extends into the interior space of the housing on the inner side of the valve. Additionally, there is no bulbous retaining prong on the inner side of the valve. The absence of the anchoring stem and retaining prong structures or any other structure in the interior space of the housing on the inner side of the valve allows the valve to fold flatter than would otherwise be possible with a structure that extends into the interior space and the flatter fold improves the inhalation airflow through the valve by minimizing the resistance to the airflow.

Figure 16B:
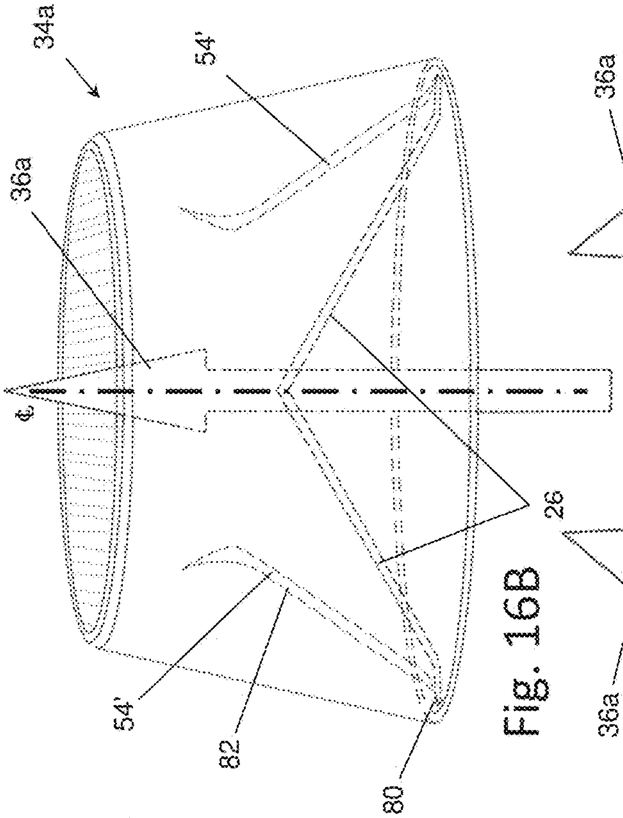
FIGS. 16A and 16B are schematic views of a nasal dilator with a duck valve and angled spars during exhalation and inhalation, respectively.
Figure 16A:
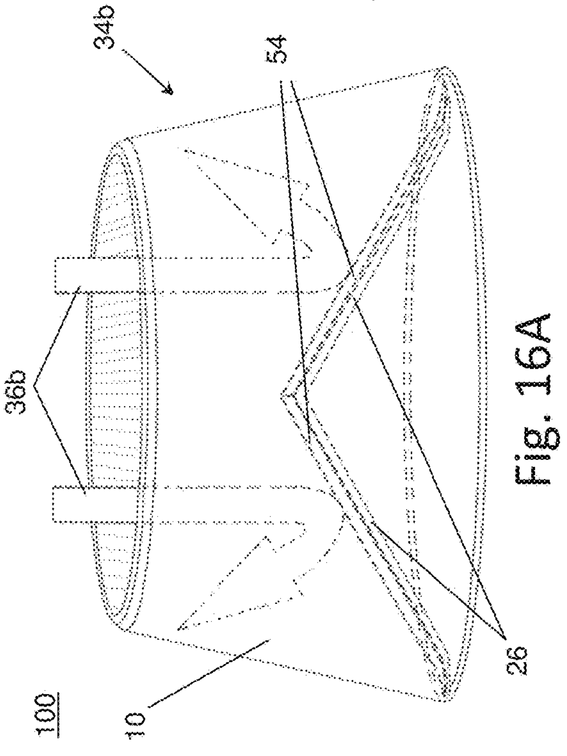

The embodiment of the NED device shown in FIGS. 16A and 16B has a duck valve 54 that operates by resting on angled spars 26 that meet at a point within the interior of the housing 10. Again, as explained above, the spars are on the outer side of the valve and do not extend into the interior space of the housing on the inner side of the valve. As with the other types of seat mechanisms described herein, the angled spars 26 prevent the duck valve flaps 54' from being forced into the blow-through position. In the closed configuration, shown in FIG. 16A, the exhalation airflow forces the valve onto the supporting seat, and the closed configuration produces backpressure. In the open configuration 34*a*, shown in FIG. 16B, the duck valve flaps 54' open to a near alignment with the housing's central longitudinal axis allowing the inhalation airflow to move freely with minimal resistance.

Figure 17B:
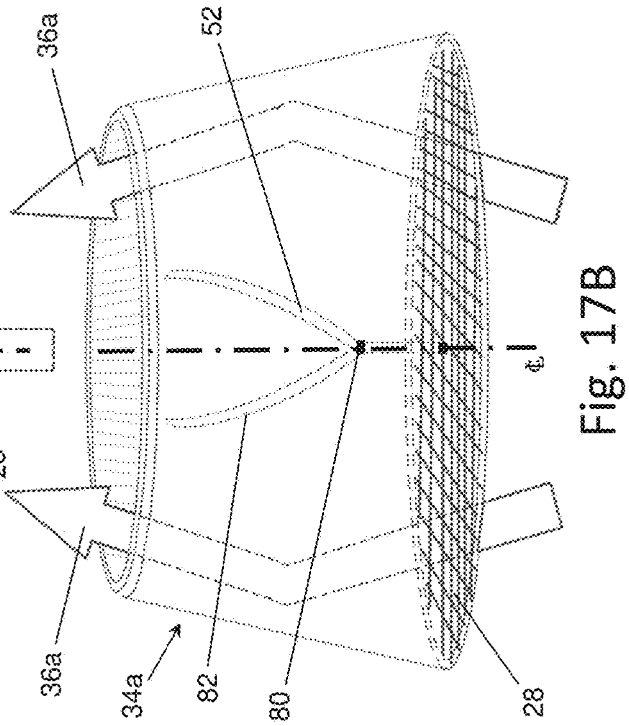
FIGS. 17A and 17B are schematic views of a nasal dilator with an umbrella valve and a screen with a central post during exhalation and inhalation, respectively.
Figure 17A:
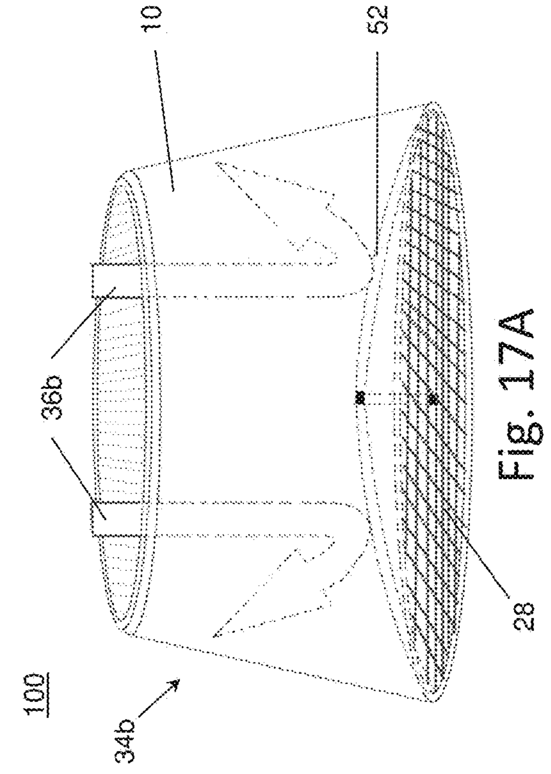

The embodiment of the NED device shown in FIGS. 17A and 17B has an umbrella valve 52 and a screen 28. During exhalation, the umbrella valve 52 spans across the interior of the housing 10 covering the bottom and rests upon the screen 28 closing off the airflow. In FIG. 17B, in the open configuration 34*a* during inhalation, the umbrella valve 52 folds together so that its flaps 80, 82 are nearly aligned with the housing's centerline axis allowing the inhalation airflow to move freely with minimal resistance.

According to the embodiments of the NED device described above and shown in the accompanying drawings, any obstruction of airflow during inhalation by the valves 14 is more than offset by the dilation of the nasal passageway by the housing. The housing 10 includes sidewalls that define a channel in the interior space for the nasal airflow and enacts the dilated state 56*a* for the nasal passage by defining an internal nasal air passageway that is greater than a constriction 210 that occurs normally in the baseline state 56*b* without inflammation or the presence of the NED device 100 in the nasal passageway 200. Since the housing both expands the nasal passage and resists passageway constriction during inhalation, the insertion 60 of a NED device will actually expand the effective nasal airway passage available during inhalation (i.e., dilation 32) in comparison to inhalation without any device at all (i.e., baseline uninflamed state of the nasal vestibule 220). Accordingly, insertion of the NED device 100 expands the effective nasal airway passage available during inhalation, in comparison to inhalation without any device at all creating a net increase of airflow. The minimal airflow resistance of the open valve is inconsequential and more than overcome by reduced resistance resulting from the dilation of the nasal passageway that is produced by the housing such that the inhalation airflow through the nasal passageway with the NED device 100 is greater than the unaided inhalation airflow through the nasal passageway without the NED device ($Q_{NEDinhalation}$>$Q_{UnaidedInhalation}$)). As explained above, the NED device's valve restricts the exhalation airflow to create a backpressure ($Q_{NEDexhalation}$<$Q_{UnaidedExhalation}$) & $Q_{NEDexhalation}$<$Q_{NEDinhalation}$), and the seat prevents the blowout condition with the blow-through of the valve by providing a stop mechanism that spans the interior space of the housing on the outer side of the valve. As shown in FIG. 19, blowout can occur in the prior art nasal EPAP devices which do not provide a seat that spans the interior space of the housing.

Figure 20:
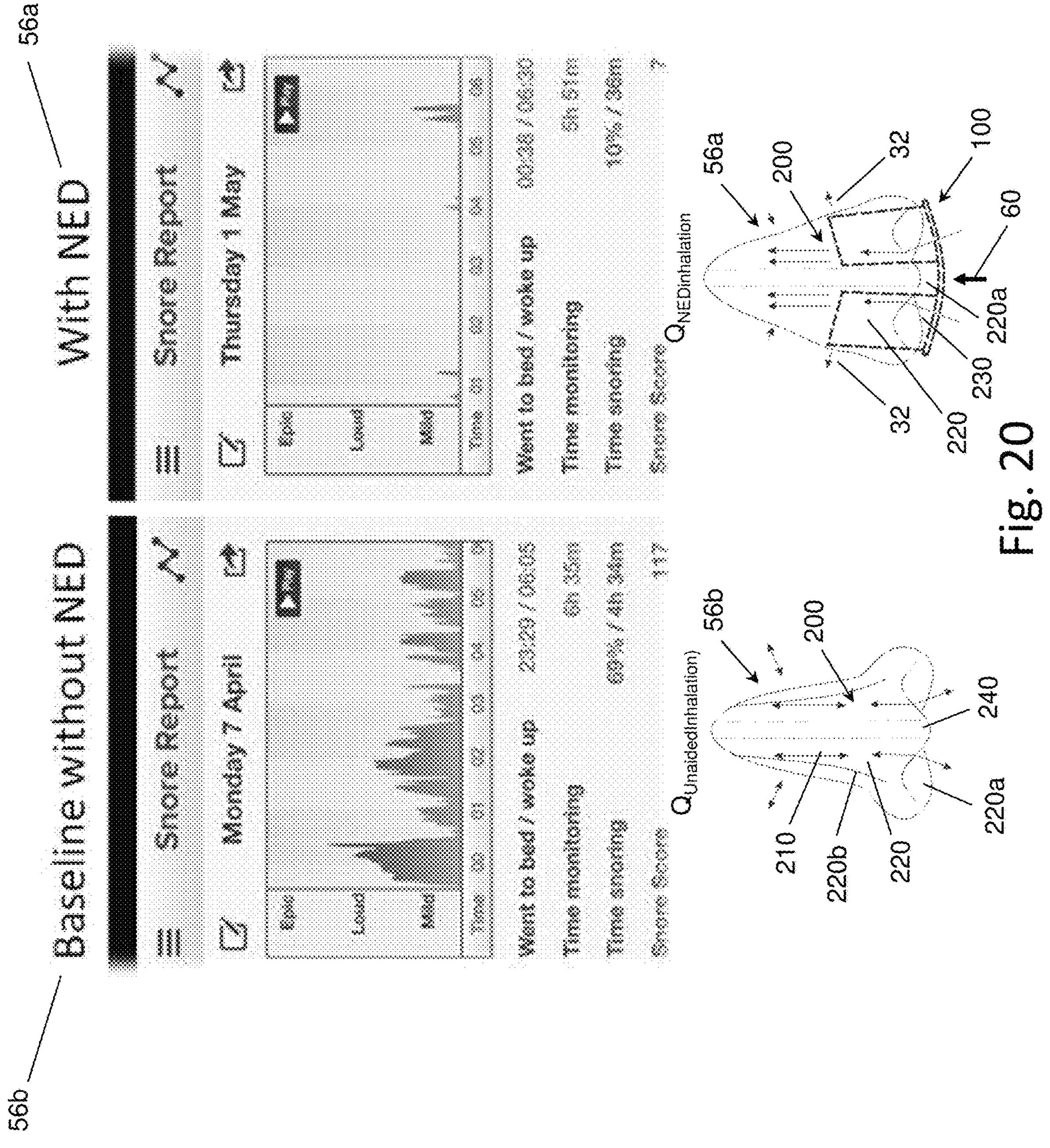
FIG. 20 illustrates schematic views of a nose and corresponding snore reports showing a time history of a person's snoring during sleep in a baseline state without any nasal device inserted in the nasal passageways and in a dilated state with the nasal dilator and valve device according to the present invention inserted in the nasal passageways.
Figure 21C:
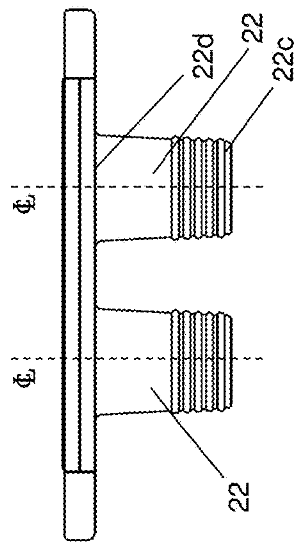
FIGS. 21A-21F illustrate views of a nasal dilator with flanges surrounding the housings and with valves clamped between a frame and the flanges.
Figure 21D:
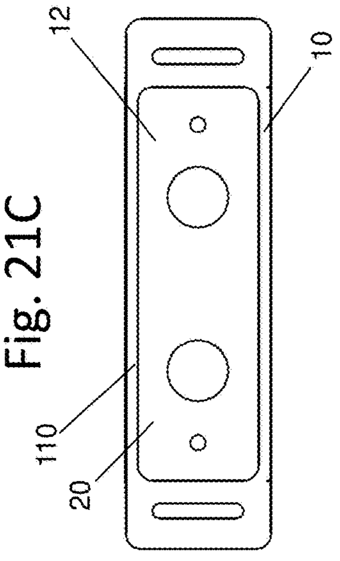
Figure 21E:
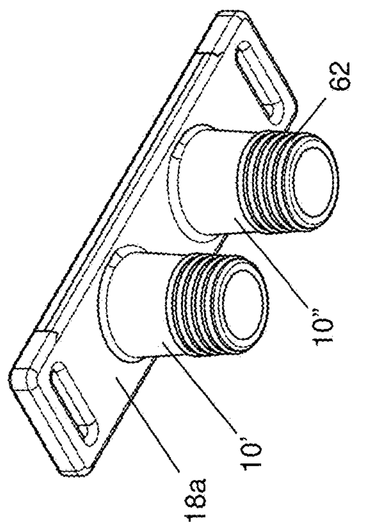
Figure 21A:
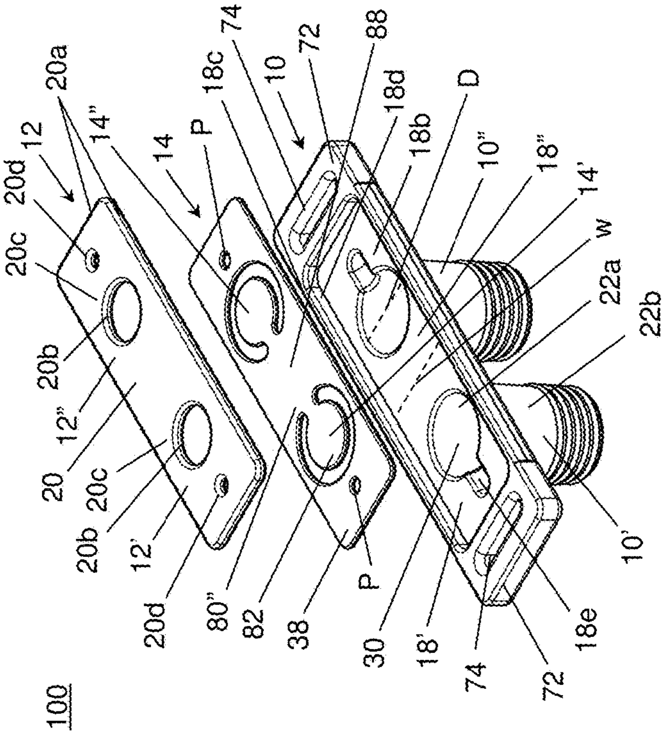
Figure 21B:
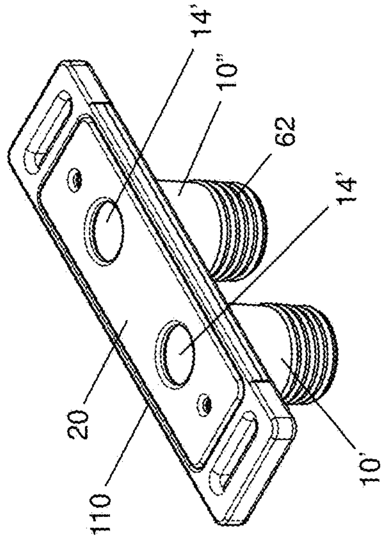
Figure 22B:
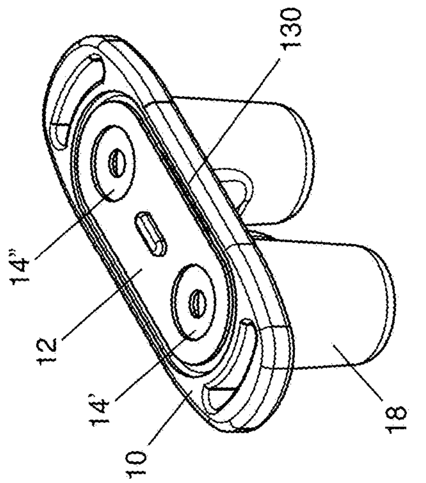
FIGS. 22A-22D illustrate views of an alternative nasal dilator with the valves clamped between the frame and flanges of the housing and an alignment key and a foam cover.
Figure 22A:
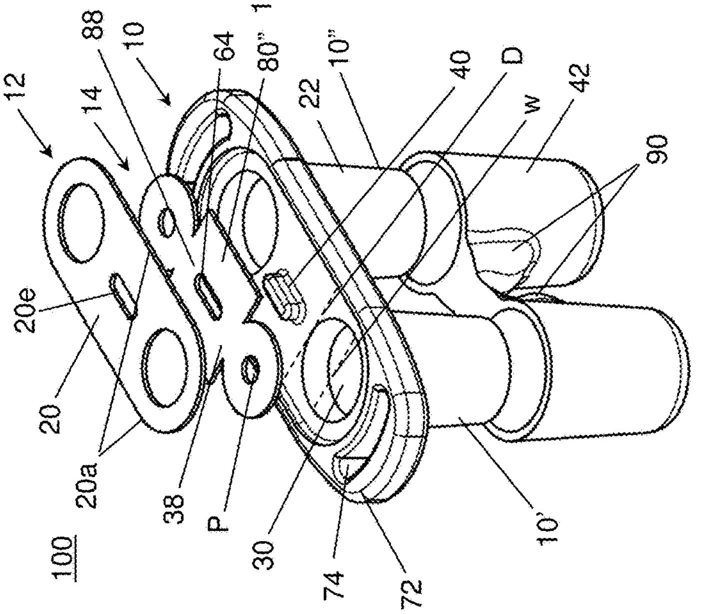
Figure 22D:
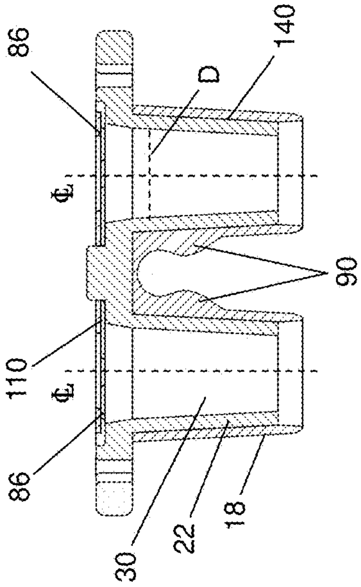
Figure 22C:
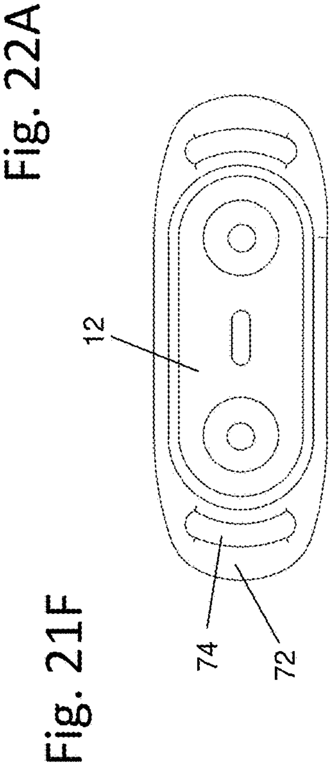
Figure 21F:
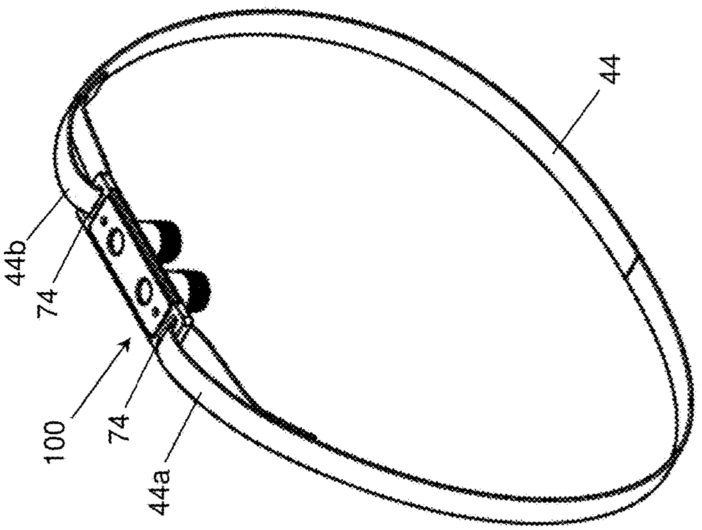

FIG. 20 illustrates schematic views of a nose and corresponding snore reports displaying the effects of the NED device 100 and its benefits when inserted in the nasal passageways in the dilated state 56*a* as compared with the baseline state 56*b* without the NED device or any other device in the nasal passageways. The corresponding snore reports are time history graphs of the level of snoring during sleep when the nasal passageways are in their dilated state with the nasal dilator and valve device inserted into the nostrils according to the present invention and in their natural state without any nasal device in the nostrils and a constriction in the nasal passageway according to the baseline state 56*b*. As shown, the time snoring is significantly decreased illustrating the benefit of the present NED device.

The NED devices shown in FIGS. 21-23 function similar to the NED devices described above with reference to the other drawings; they dilate nasal passageways to remove a constriction 210 in the baseline uninflamed state of the nasal vestibule 220. In these embodiments, the NED device 100 has a pair of housings 10', 10" with flanges 18', 18" at their respective outer ends, a rigid plate 20 connected to the housings through the flanges, and a flexible membrane 38 having a pair of valves 14', 14" and a corresponding mounting portion that is held in a clamped engagement 110 between the rigid plate and the flanges. Preferably, the valves include an exhalation port (P) that limits the exhalation airflow ($Q_{NEDexhalation}$) through the respective valves. The housing assembly, rigid plate, and valve assembly may be bonded to each other, such as with a silicon adhesive or by fusing the parts together with heat welding, or they may be releasably connected to each other so the rigid plate can be detached from the housing and the valve assembly can be removed and replaced. The separable plate and the replaceable valves are useful for replacing worn out valves and also allow for selecting valves from a set of valves 14*a*, 14*b*, 14*c* having the same shape around their periphery with different sized exhalation ports (Pa, Pb, Pc) which are discussed in detail below.

In these clamped valve NED devices, each housing 10 has an elongated tube 22 with a tubular sidewall 10*c* that has an interior surface 22*a*, an exterior surface 22*b*, an inner end 22*c*, and an outer end 22*d*. The interior surface surrounds an interior space 30 and extends along a centerline axis (℄) between the inner end and the outer end. The exterior surface for each of the pair of housings is configured to be positioned within a corresponding one of the nasal passageways, and an insertion of the pair of housings into the respective nasal passageways expands the nasal passageways from the baseline uninflamed state without the housings inserted in the nasal passageways to a dilated state with the housings inserted in the nasal passageways. The tubular sidewall produces a dilation 32 of the corresponding one of the nasal passageways in the dilated state with the interior space of the respective housings being greater than the constriction of the corresponding nasal passageways in the baseline uninflamed state.

The exterior surface 22*b* of each of the housings proximate to the outer end preferably includes the flanges 18', 18" that surround the corresponding tubular sidewall and extend substantially perpendicularly away from the centerline axis. Each flange 18 has an inward facing surface 18*a*, an outward facing surface 18*b*, and an outer sidewall 18*c* and remains outside 230 the nasal vestibule when the tubular sidewalls of the housings are inserted in the corresponding nasal passageways. The outer sidewall preferably forms a lip around the periphery of the flanges so that the outward facing surface is recessed, and the rigid plate fits in the recessed space of the outward facing surface. Additionally, the sidewall may have an interior groove 18*d* that provides a snap fit detachable connection 120 for releasably connecting the rigid plate to the flange. As explained below with reference to FIG. 23, the rigid plate can alternatively fit over the outer sidewall of the flange with a snap-fit detachable connection between the rigid plate and the flange. Additionally, as indicated above, an adhesive or other fastener or a heat weld can provide a fixed connection 130 for permanently connecting the rigid plate to the flange.

The inward facing surface is adjacent to an exterior side 220*a* of the nasal vestibules when the housings are inserted in the nasal passageways. The flange for each of the housings is preferably connected to the other flange through a bridge section 16' that preferably has a width (w) greater than a diameter (D) of the tubular sidewall, i.e., w>D. The larger width of the bridge section can be important in connecting the separate rigid plate to the flange of the housing and strengthening the NED device assembly to provide the dilation to the nasal passageways. The exterior surface of each of the housings or the foam cover proximate to the inner end may include a series of protruding ridges 62 as shown in FIG. 21 that engage the inner walls 220*b* of the nasal vestibule or may have another type of protrusion such as the bumps 90 shown on the foam cover in FIG. 22 that are designed to grip the septum within the nasal vestibule, preferably gripping the columella 240. As shown in FIG. 23, the protrusions may be positioned toward the inner end of the housing. In general, the protrusions 62, 90, 146 help secure the housing within the nasal vestibule.

The rigid plate 20 has a pair of seats 12', 12" and a plurality of sides 20*a*. Each of the seats has an aperture 20*b* and an edge region 20*c* around the aperture. For the NED devices in which the rigid plate is secured in the recessed outward facing surface, such as shown in FIGS. 21 and 22, the rigid plate can be secured to the flange by an adhesive or other fasteners or the sides of the rigid plate can have a snap-fit connection within the corresponding interior groove in the outer sidewall of the flanges in the respective housings. Each aperture is substantially centered around the centerline axis in the interior space of the first housing. The edge region is closer to the centerline axis than the interior surface and covers a portion of the interior space proximate to the interior surface. Although the rigid plate shown in FIGS. 21-23 is a solid plate with circular apertures, it will be appreciated that the rigid plate could be a frame with one or more polygonal shaped apertures or other irregularly shaped apertures similar to the frames shown in FIGS. 1-6, 9-11, 13, 15, 16, and 18 or could be formed from screen material shown in FIGS. 12, 14, and 17. The rigid plates and flexible membranes in FIGS. 21-23 are separate from the housings and are connected together to form the NED devices, and it will be appreciated that the seats and valves can be integrally formed with the housings such as described with reference to the NED device described above with reference to FIG. 13.

The pair of valves formed in from the flexible membrane are preferably a type of flap valve 46 connected through a body section 88. Each of the valves has a mounting portion 80" and a free end 82. The mounting portion and the body section are held in the clamped engagement between the rigid plate and the outward facing surface of the flanges. The free end extends from the mounting portion into the interior space of the corresponding one of the housings, and the body section extends from the mounting portion to a side location proximate to the outer sidewall. Each one of the valves has an open configuration when an inhalation airflow passes from the outer end to the inner end and a closed configuration when an exhalation airflow passes from the inner end to the outer end. The valves restrict the exhalation airflow in the closed configuration, and the dilation in the nasal passageways and the open configuration allow the inhalation airflow to pass through the interior space of the respective housings in the dilated state more freely than an unaided inhalation airflow which passes through the corresponding nasal passageways in the baseline uninflamed state which has a restriction when there is no device providing any dilation.

In the closed configuration, the free end 82 of each of the valves 14 contacts the rigid plate 20, and the edge region 20*c* around the aperture 20*b* in the rigid plate engages and supports the valves at least around the periphery 86 of the free end. In the open configuration, the free end of each of the valves is displaced from the corresponding aperture in the rigid plate. To ensure that there is no interference to the inhalation airflow freely passing through the interior space of the housings, there is no structure other than the valves positioned in the interior space of the housing. It is important that no structure is positioned in the interior space of the first housing between the first valve and the inner end of the first housing, inclusive, because any additional structure at the location of the valve, at the inner end, or anywhere between in the interior space could result in a constriction that could interfere with the inhalation airflow. Although it is possible that some aerodynamically crafted structure may be positioned within the interior space without interfering with the inhalation airflow, there is no need for any such structure in the embodiments of the present invention and it is preferred that there not even be any aerodynamically crafted structure in the interior space.

The versions of the NED device 100 shown in FIGS. 21 and 22 also preferably include tabs 72 extending from the lateral ends of the flanges. The tabs each have a slot 74 which allow a head strap 44 to be threaded through the slot and the ends 44*a*, 44*b* of the head strap are fastened around the tab as shown in FIG. 21F. The head strap can be adjustable and is particularly useful when a person is sleeping for holding the NED device in place within the nostrils.

As shown in FIGS. 22 and 23, a foam cover 42 can have a friction fit 140 over the housings to help in securing the NED device in the nostril and help with the comfort of the NED device. It will be appreciated that the foam cover is preferably a replaceable structure that fits over the tubular sidewalls of the housings that are provide the structural support to dilate the nostrils and are less likely to wear out as compared to the valves and the foam cover. The center portion of the flange in embodiment in FIG. 22 preferably includes a projection 40 that protrudes through a hole 64 in the flexible membrane and a corresponding hole 20*e* in the rigid plate. The projection can be slightly elongated so that it serves as an alignment key for easy and accurate placement of valves within the flange. The projection may have an enlarged head that provides a snap-fit detachable connection for the hole in the rigid plate and/or the shaft of the projection may provide a friction fit connection with the hole in the rigid plate. It will also be appreciated that the external shape of the valve and the rigid plate can be formed in the shape of the recessed outward facing surface so that they are aligned by the outer sidewall of the flange.

Figures 23A, 23B, 23C, 23D, 23E, 23F:
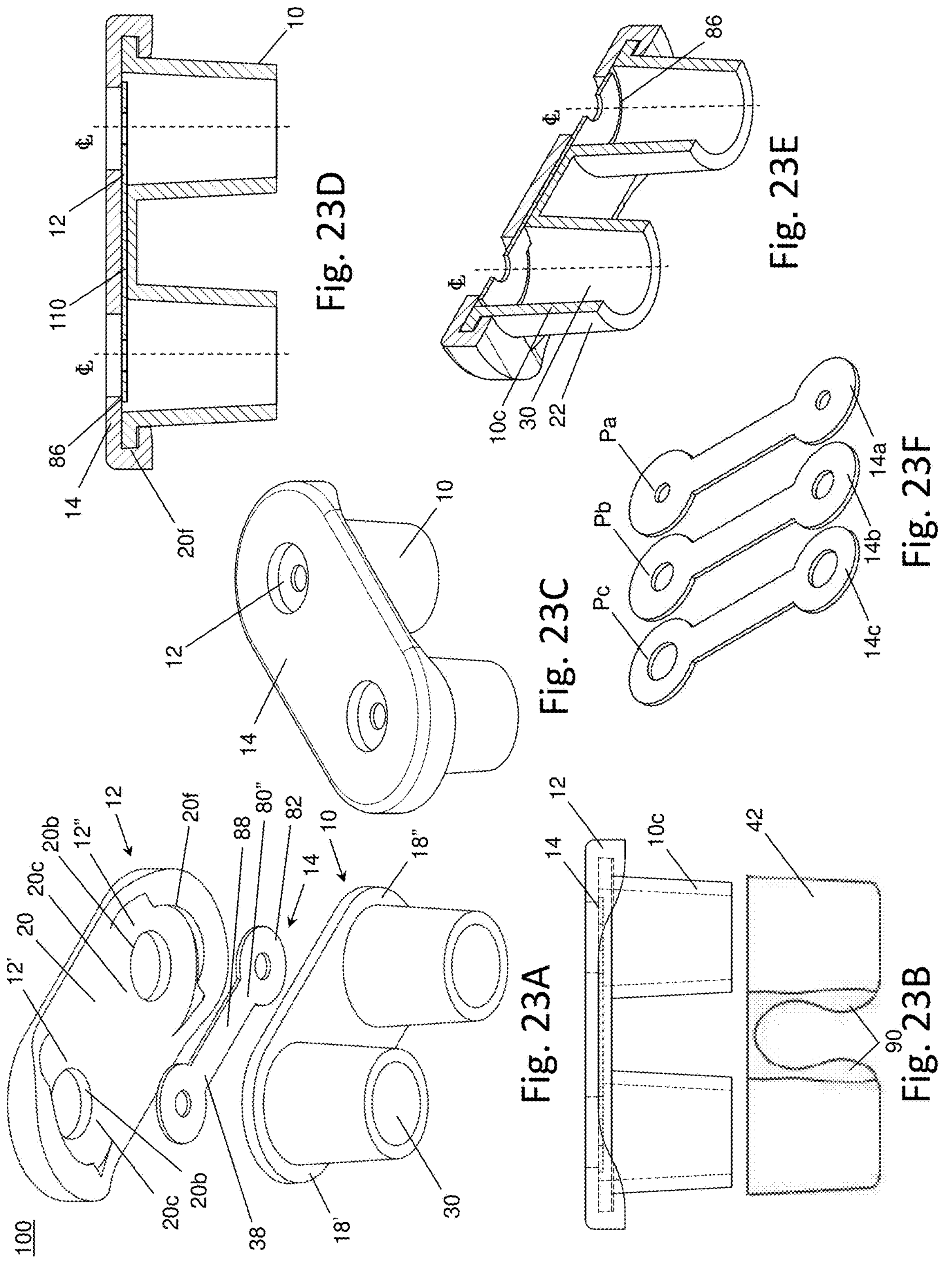

The NED device shown in FIG. 23 has a rigid plate that fits over the outer sidewall of the flange and provides a snap-fit connection between the rigid plate and the flange so that the rigid plate is detachable from the flange and so that different valves can be placed between the rigid plate and the flange. In this embodiment, the outer sidewall of the flange is held within a groove 20*f* of the rigid plate. The detachable rigid plate is beneficial for replacing worn out valves and is also helpful in optimizing the EPAP strength for a user's needs. For example, as shown in FIG. 23F, valves that have the same outer dimension for the flexible membrane can have different sized exhalation ports that allow the users or medical professionals to modify the EPAP strength of the NED device. The smaller exhalation port (Pa, 2 mm diameter) allows less exhalation air through the valve resulting in more EPAP resistance as compared to a standard size exhalation port (Pb, 3 mm diameter) while the larger exhalation port (Pc, 4 mm diameter) allows more exhalation air through the valve resulting in less EPAP resistance as compared to the standard size exhalation port. It will be appreciated that varying sizes of exhalation ports can also be used with the other embodiments, including the NED device shown in FIG. 21 which has the exhalation recess 18*e* in the flange, the exhalation port (P) in the corresponding section of the flexible membrane, and an exhalation aperture 20*d* in the corresponding section of the rigid plate. Furthermore, it will also be appreciated that the exhalation port in the NED device shown in FIG. 21 is preferably offset from the valve and aligned with the exhalation recess which provides fluid connectivity from the interior space to the exhalation apertures in the rigid plate. However alternative embodiments, such as shown in FIG. 25, may situate the exhalation port (P) within the periphery 86 of the free end of the valve that are aligned with the exhalation recesses and apertures. In either embodiment the valve will close during exhalation to create back pressure while a small amount of air flows through the exhalation port.

The replaceability of valves and the ability to vary valves with different EPAP strengths are beneficial features of the present NED device. Valves can wear down and lose performance so the ability to replace valves allows a user to maintain optimal performance without having to discard the housing and rigid plate. In addition, the ability for a single housing-rigid plate pair to use valves with different sized exhalation ports (Pa, Pb, Pc) allows for the titration of the EPAP to the particular needs of a user, i.e., a smaller exhalation port (Pa<Pb) has more EPAP resistance and provides a stronger treatment for more severe SDB, and a larger exhalation port (Pc>Pb) has less EPAP and provides a lower treatment for less severe SDB. The larger the exhalation port, the less EPAP resistance, and the better suited the valve would be for more mild forms of SDB or those persons who find more comfort with less backpressure. The smaller the exhalation port, the greater the EPAP resistance, and the better suited the valve would be for SDB that requires a greater degree of EPAP resistance to achieve efficacious outcomes.

An example of the use of valves with different EPAP resistance helps explain the importance of the replaceable valves clamped between a rigid plate that is detachably connected to the housing's flange. Consider a person who has moderate SDB who tries a NED device with a valve with a medium strength exhalation port. If the user continues to snore more than desired, the user can simply detach the flange from the housing and replace the valve with the medium strength EPAP resistance with a valve that has a higher strength EPAP resistance. However, another user may feel like the medium strength EPAP resistance valve was too strong and felt uncomfortable to breath against in which case the user can simply detach the flange from the housing, remove the old valve and replace it with a valve having a lower strength EPAP resistance. Also, if a valve becomes less effective during an extended period of use or otherwise wears out, the user can reuse the flange and body to which the user has become accustomed and only replace the old valve with a new valve. With the present invention, the user can even decide to use the NED device just for dilation and without any EPAP resistance by removing the valve from the device. It will be appreciated that these improvements provided by the present invention are not available in prior art dilators or separate EPAP devices nor have they even been considered in prior art nose plugs that are designed to be used when a person is awake.

The NED devices shown in FIGS. 24 and 25 function similar to the NED devices described above with reference to the other drawings while improving on the same. These alternative embodiments include a housing 10 to dilate the nasal passageways to remove constriction in the baseline uninflamed state of the nasal vestibule and further improve on the other NED devices by allowing the user to adjust exhalation airflow with a dial assembly 92. With adjustable exhalation airflow via the dial assembly, a user can tailor the NED device to their desired therapeutic need as well as comfort without valve replacement. Although the particular description of these alternative embodiments is made with reference to a single housing, dial and valve, it will be appreciated that a second housing, dial and valve can be provided and connected together with a bridge section 16 as particularly discussed above and shown in the figures. The bridge also simplifies the usage of the NED device by providing a gripping portion that remains outside of the nose that helps in inserting the NED device into the nasal passageway and also helps in the removal of the NED device from the nasal passageway.

In these embodiments, the dial assembly 92 is situated proximate to the outer end 22*d* of the housing and includes a fitting 94 sandwiched between the outer end of the housing and a dial actuator 96 that is rotably connected to the fitting outside of the nasal passageway opposite from the housing. The dial actuator includes a central aperture 98 and the fitting includes an inhalation port 102 which are both coaxially aligned with the interior space 30 along the centerline axis (℄). The fitting includes an exhalation aperture 20*d* proximate to its perimeter which aligns with an open section 104*a* within the tubular sidewall of the housing according to the NED device shown in FIG. 24 and an open section 104*b* in the dial actuator according to the NED device shown in FIG. 25. The dial actuator and the fitting each further include an inner surface 96*a*, 94*a* an outer surface 96*b*, 94*b* with the inner surface of the dial actuator connecting to the outer surface of the fitting. The inner surface of the fitting is situated proximate to the outer end of the first housing and is proximate to the outward facing surface 18*b* of the flange 18 surrounding the tubular sidewall of the housing when included. Accordingly, the inward facing surface 18*a* of the flange is adjacent to the exterior periphery of the nasal vestibule without any interference from the dial assembly.

In operation, the exhalation airflow is increased or decreased while the valve closes the inhalation port by rotating the dial actuator between a fully open position 106*a* with an unobstructed 108*a* exhalation aperture to a partially open position 106*b* that at least partially obstructed 108*b* exhalation aperture. Obstructing the exhalation aperture allows less exhalation air through the NED device resulting in more EPAP resistance as compared to an unobstructed exhalation aperture in the fully open position which results in less EPAP resistance. Conversely, the actuator can be rotated into a fully closed position 106*c* with the exhalation aperture fully obstructed 108*c*.

The valves 14 of the NED devices shown in FIGS. 24 and 25 each include a fixed end 80 and a free end 82 such that during inhalation the free end moves towards the housing's inner end into an open configuration, allowing air to flow freely through the dilated nasal passageway. During exhalation, the valve is in its closed configuration, blocking airflow from passing from the interior space through the inhalation port, and a back pressure is created while a small amount of air flows out of the nasal passageway through the exhalation aperture in the NED device shown in FIG. 24 and through exhalation recess, port and aperture in the NED device shown in FIG. 25.

The fixed end of the valve of the NED device shown in FIG. 24 is held in a clamped engagement 110 between the dial assembly and the fitting whereas the fixed end of the valve of the NED device shown in FIG. 24 is held in a clamped engagement between the outer end of the housing and the fitting. However, in each embodiment, the valves have a fixed end 80 that remains stationary and free end 82 coaxially aligned with the interior space and the inhalation port which opens and closes according to the general description of the valves above. As shown in the accompany drawings and with regard to the exhalation airflow moving from the inner end of the housing towards the dial assembly positioned on the outer end outside of the nasal vestibule, it will be appreciated that the valve is downstream of the exhalation apertures in the embodiment shown in FIG. 24 and upstream of the exhalation apertures in the embodiments shown in FIG. 25 as well as the embodiment shown in FIG. 21.

As explained with reference to the other valves discussed above, the fixed end may have an integrally formed portion with either the housing or dial assembly, may be formed separately with a mounting portion that is connected to either the housing or the dial assembly by a mechanical means, such as with a separate fastener or an adhesive layer or by a clamped engagement as referenced above, or may be heat welded together. The flaps of the valve can move freely at a free end by a pair of sides that extend from the fixed end to the free end. Preferably, the sides of the flaps have a curvature conforming to the shape of the interior surface of the housing but may also include the exhalation ports as discussed herein.

The NED device shown in FIG. 24 has an open section 104*a* in the housing proximate to the outer end whereas the NED device shown in FIG. 25 has an open section 104*b* in the dial actuator radially spaced towards the periphery 112 of the actuator from the central aperture 98. In both embodiments, the actuator rotates such that the exhalation aperture is unobstructed 108*a* and in the fully open position 106*a* when the open section is aligned with the exhalation aperture, is partially obstructed 108*b* and in a partially open position 106*b* when the open section is partially removed from the exhalation aperture, and is fully obstructed 108*c* and in a fully closed position 106*c* when the open section is fully removed from the exhalation aperture.

The open section of the NED device shown in FIG. 24 is situated within a circumferential section 114 of the housing's tubular sidewall proximate to the outer end. The circumferential section includes a circumferential groove 116*a* recessed a depth (DG) from the interior of the sidewall. The groove intersects with the open section which preferably has a rectangular slot 116*b* shape, as depicted in FIG. 24B.

Figures 26A, 26B, 26C, 26D, 27A, 27B, 27C:
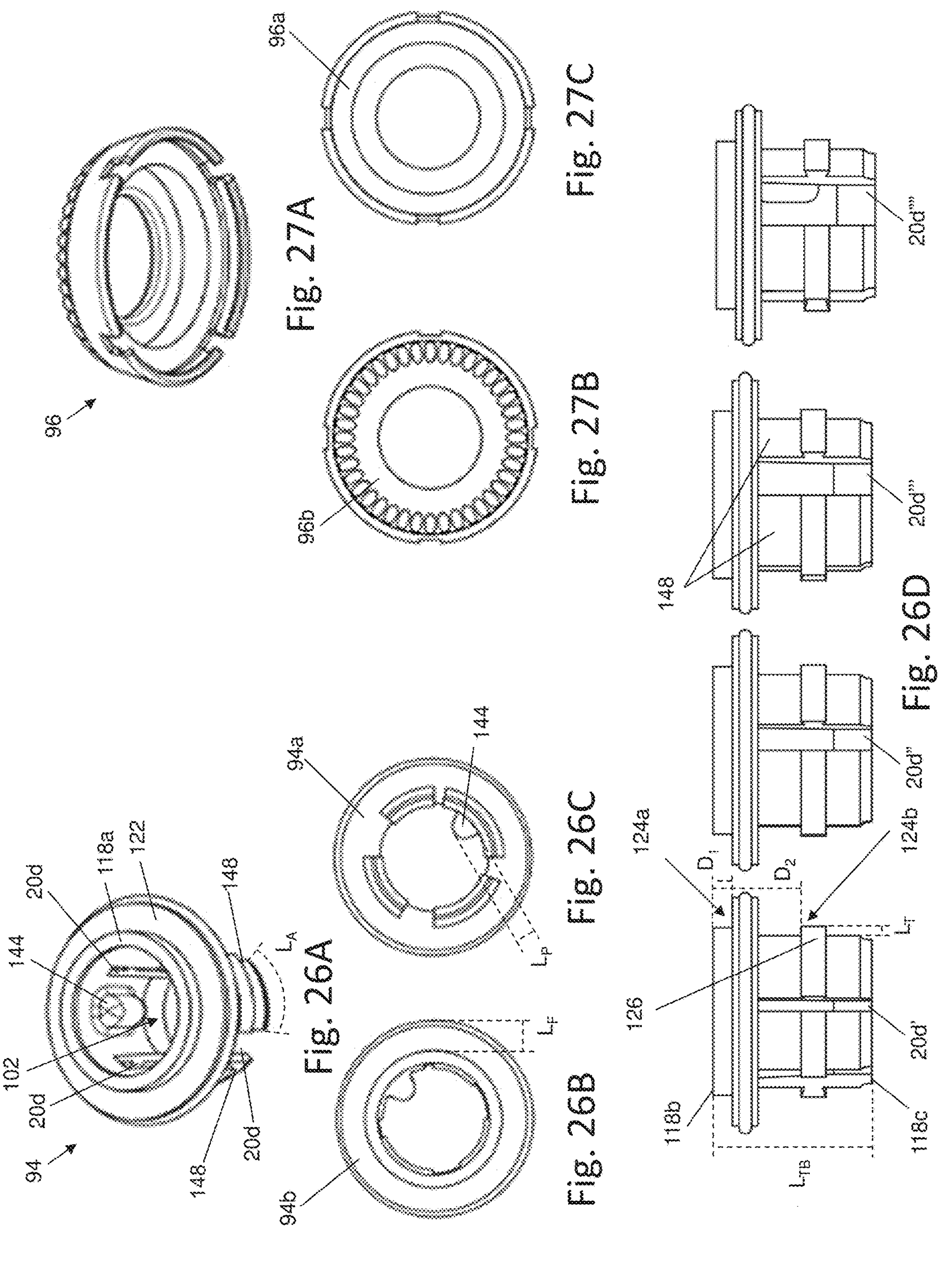
FIGS. 26A-26D show details views of the fitting in the nasal dilator according to the embodiments shown in FIG. 24.
FIGS. 27A-27C show details views of the dial actuator in the nasal dilator according to the embodiments shown in FIG. 24.

The fitting of the NED device shown in FIG. 24 includes a tubular body 118 that is received within the circumferential section housing the slot and groove. The tubular body includes a body sidewall 118*a* that extends a length ($L_{TB}$) from an outer edge 118*b* to an inner edge 118*c* situated within the interior space when the tubular body is received therein. The body sidewall surrounds the inhalation port 102 which extends between the inner edge and the outer edge and the exhalation apertures 20*d* positioned within the body sidewall. A circumferential flange 122 protrudes a flange length (LF) from the exterior side of the body sidewall at a location 124*a* spaced a first distance ($D_1$) from the outer edge. When assembled, the circumferential flange seats against the outer end of the housing as shown in FIG. 24A and illustrated in FIG. 24C. A circumferential tongue 126 also protrudes a tongue length ($L_T$) from the exterior side of the body sidewall at another location 124*b* spaced a second distance ($D_2$) from the outer edge that is greater than the first distance ($D_1<D_2$) such that the tongue is positioned between the circumferential flange and the inner edge as shown in FIG. 26D. When assembled, the circumferential tongue is received within the circumferential groove. Preferably, the exhalation aperture within the sidewall preferably extends from the inner edge to the circumferential flange but it will be appreciated that the aperture need only be situated within the sidewall at a location that aligns with the open section in the housing.

Figure 24D:
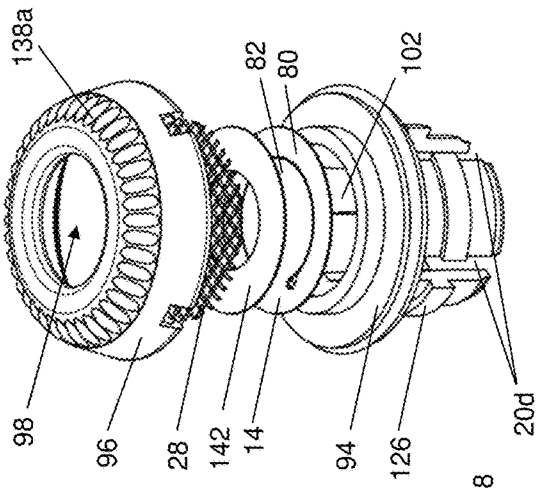
FIGS. 24A-24E illustrate views of a nasal dilator with a dial assembly for adjusting exhalation airflow without valve replacement.
Figure 24E:
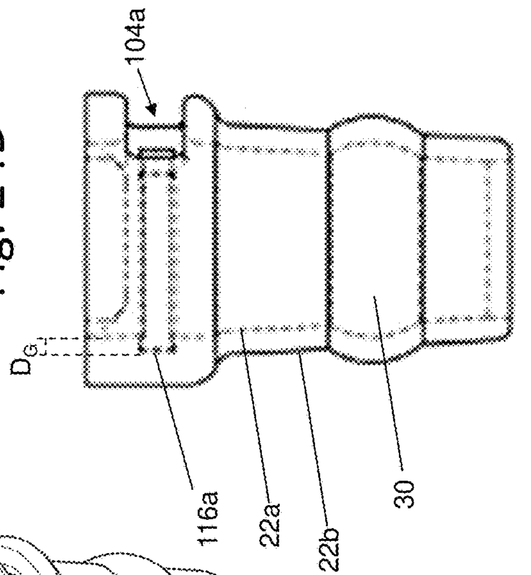
Figure 24C:
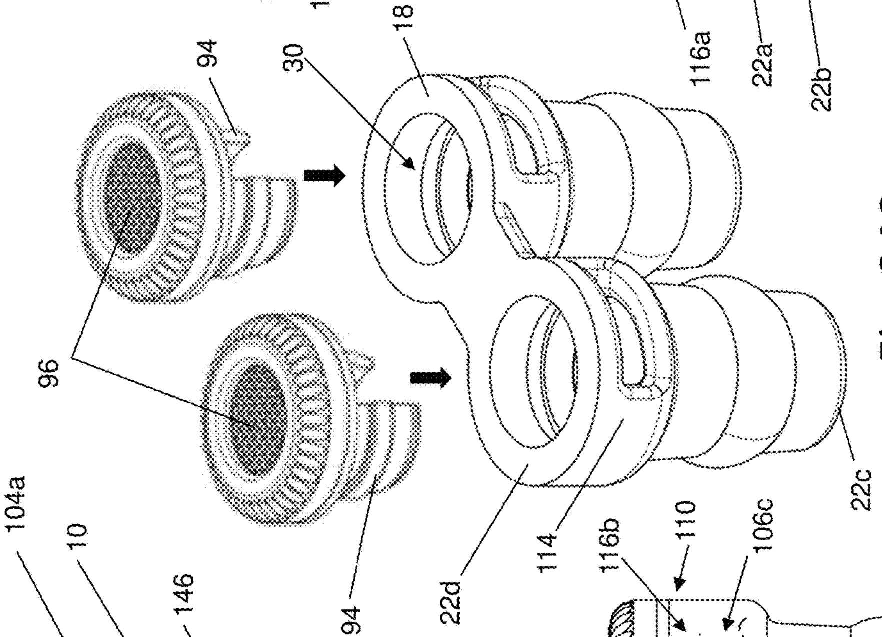
Figure 24A:
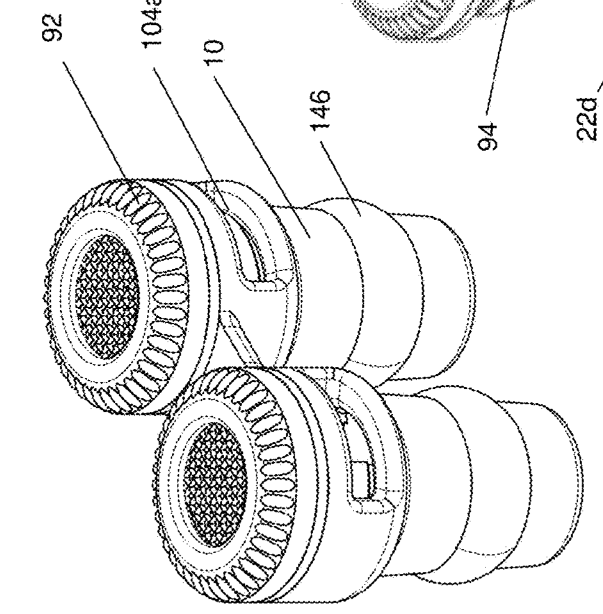
Figure 24B:
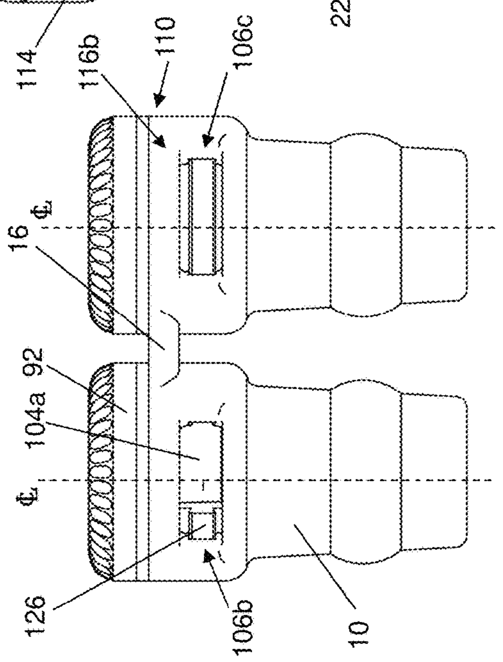

In operation, the inner surface of the dial actuator rotably connects with the outer edge of the fitting and rotates the tubular body around the center axis between the open and closed positions with the exhalation aperture being aligned with or removed from the slot. When fully or partially closed, it will be appreciated that the housing obstructs at least a portion of the aperture and at least a portion of the tongue is rotated into the slot to as shown in FIG. 24B. In this position the exhalation aperture opening is reduced or altogether closed to increase EPAP resistance as explained above. Conversely, when fully opened, it will be appreciated that the slot is positioned around the exhalation port as illustrated in FIG. 25B and EPAP resistance is decreased.

The fitting 94 of the NED device shown in FIG. 25 particularly includes a planar cover 128 that connects to the housing proximate to the outer end, which preferably includes the flange 18 as discussed above with reference to FIG. 23. Like the rigid plate in the alternative the embodiments, the planar cover 128 can fit over the outer sidewall of the flange with a snap-fit detachable connection and sandwiches the valve between the outer end of the housing and planar cover. Alternatively, the planar cover can connect to the housing with the valve sandwiched therebetween according to any of the other means discussed herein. An inhalation port 102 is provided within the planar cover and aligns with the interior space of the housing while the exhalation aperture 20*d* is situated between the perimeter of the inhalation port 102 and the edge of the cover and is aligned with the exhalation port of the valve and exhalation recess of the housing. The plan area 132 of the inhalation port and exhalation aperture is circumscribed by the periphery 134 of the housing's interior surface proximate to the outer end with the sides of the cover 128*a* extending beyond the periphery of the outer end and preferably mating against the flange as discussed above to sandwich the valve in place. Furthermore, the periphery 86 of the free end of the valve extends beyond the perimeter of the inhalation port such that the free end of the valve closes the inhalation port during exhalation while a small amount of air escapes through the exhalation port (P) and subsequently through the exhalation aperture, when opened.

Figure 25A:
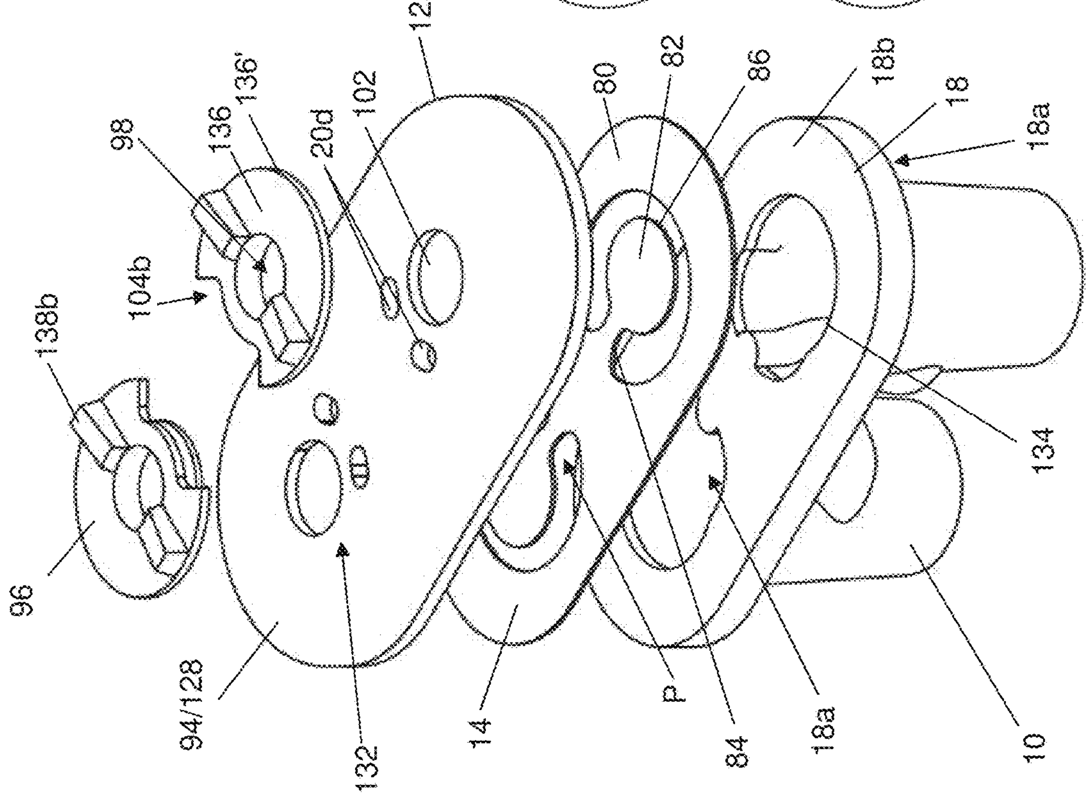
FIGS. 25A and 25B illustrate views of an alternative nasal dilator with a dial assembly for adjusting exhalation airflow without valve replacement.
Figure 25B:
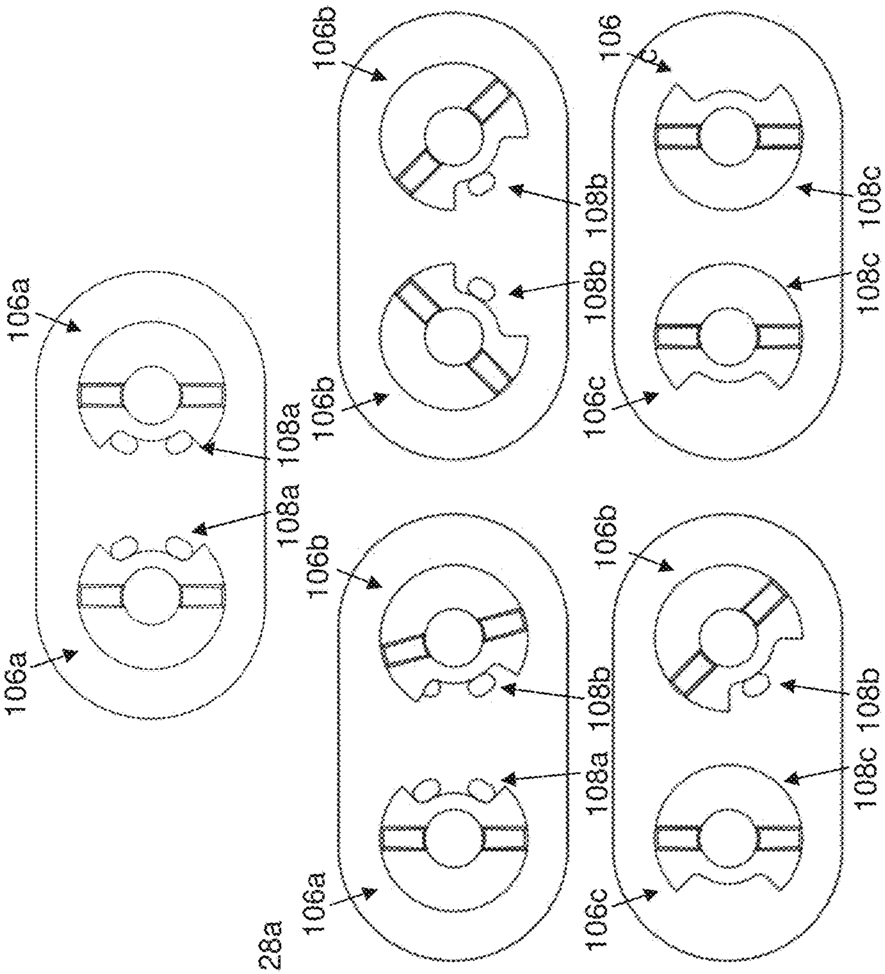

To control exhalation airflow with the dial assembly shown in FIG. 25, a dial actuator 96 having a dial flange 136 rotably connects to the planar cover. The dial actuator includes a central aperture 98 aligned with the inhalation port and interior space and an open section 104*b* proximate to the perimeter 136' of the flange. As shown in FIG. 25B, the dial actuator rotates between various positions 106*a*, 106*b* and 106*c* to cover and uncover portions of the exhalation aperture 108*a*, 108*b* and 108*c* and subsequently control exhalation resistances and EPAP strength by adjusting airflow through the NED device during exhalation. Notably, in this alternative embodiment the fitting remains fixed in place and the dial actuator rotates in comparison to the embodiment discussed above and shown in FIG. 24 wherein both the fitting and the dial actuator rotate.

To provide an improved bearing surface on the outer surface of the dial actuator, a peripheral grip 138 is included around the aperture in both dial assembly embodiments. As shown in FIG. 24D, the peripheral grip can be a series of ridges 138*a* around the circumference of the aperture or may include tabs 138*b* on opposite sides of the aperture as shown in FIG. 25A. In either embodiment the peripheral grip allows the user to more easily rotate the dial actuator and adjust the EPAP amount.

As shown in FIGS. 24 and 25 it will also be appreciated that multiple exhalation apertures can be included in the dial assembly for more controlled adjustments. For example, FIG. 26D shows four (4) exhalation apertures 20*d'*, 20*d''*, 20*d'''* and 20*d''''* within a single fitting that each have a known opening dimension while FIGS. 25A and 25B show two (2) exhalation apertures within the planar cover of each NED device. Correlating the known opening dimension with device efficacy allows for more controlled adjustments in comparison to experimenting with subtle rotations of the dial to slightly open or close the exhalation apertures by an unknown degree. Although these NED devices allow for incremental adjustments, embodiments with multiple exhalation apertures having fixed dimensions also allow for controlled and measurable adjustments.

With particular regard to the embodiment shown in FIG. 26D, the apertures opening dimensions are preferably unequal while the difference between opening dimension is standardized between each aperture, such as a 1 mm difference between each aperture, and indicia on the dial actuator indicates which aperture is rotated into the open position. In this embodiment lands 148 circumferentially space adjacent apertures from one another by corresponding arc lengths ($L_A$) which are unequal to one another considering the differing opening dimensions of each aperture. Conversely, the apertures shown in FIG. 25 are the same size.

To prevent blowout of the valve during exhalation a valve support 28 made from a porous material, such as a mesh screen, covers the inhalation port and opening of the interior space. Notably, the valve support does not restrict the inhalation or exhalation airflow but prevents the free end of the valve from blowing out through the inhalation port as exhalation airflow passes from the inner end of the housing towards the outer end.

A gasket 142 is provided in the alternative embodiment shown in FIG. 24D to produce a stronger seal when the valve is closed. As shown in the exploded view, the gasket is circumferential in shape and is adjacent to the periphery of the free end such that the free end seals against the gasket rather than the interior surface of the dial actuator. With the gasket included, exhalation resistances and EPAP strength is more accurately controlled because the likelihood of exhalation airflow seeping out of the closed valve is reduced. Conversely, a prong 144 on the inner end of the body can be included on the housing's interior space to prevent the valve from fully opening during inhalation and to reduce the likelihood that the valve surface will stick to the interior sidewall of the housing. As shown in FIG. 26C, prong extends a length ($L_P$) into the interior space that is less than half the diameter of the housing's tubular sidewall ($L_P$<1/2 D) so as not to block inhalation airflow when the valve is open.

As with other NED devices described herein, the devices having a dial assembly may also include a protrusion 146 around the exterior surface of the housing that engage the inner walls of the nasal vestibule or may have another type of protrusion such as the bumps 90 shown on the foam cover in FIG. 22 that are designed to grip the septum within the nasal vestibule, preferably gripping the columella 240. As shown in FIG. 23, the protrusions may be positioned toward the inner end of the housing. In general, the protrusions 62, 90, 146 help secure the housing within the nasal vestibule.

The ability to vary EPAP strengths with the dial without having to take the device out or change valves is a beneficial feature of the NED embodiments shown in FIGS. 24 and 25. The dial assembly can cover, to variable amounts, the size of the exhalation apertures which allows for the precise tailoring of the exhalation resistance to the particular needs of a user. For example, rotating the dial actuator into a position where more of the exhalation aperture is obstructed creates smaller overall exhalation aperture surface area which provides more exhalation resistance and thus more EPAP which is associated with treatment for more severe SDB, such as more severe snoring or OSA. Rotating the dial actuator into a position that obstructs less of the exhalation aperture creates larger overall exhalation aperture surface area which provides less exhalation resistance and thus less EPAP and is associated with treatment for less severe SDB corresponding with more mild snoring or OSA. In addition to tailoring exhalation resistance to achieve optimal therapeutic outcomes, this precise tailoring also allows a user to tailor the NED device to comfort. Too much exhalation resistance, while perhaps optimal from a therapeutic perspective, can be too uncomfortable for some people. With the use of the dial assembly to individualize exhalation resistance, a user can find the perfect balance between therapeutic outcome and comfort.

The dial assembly also enables EPAP adjustments without taking the device out of the user's nose. For example, consider a person who is a loud snorer and consistently disturbs their bedtime partner's sleep. This snorer can use a NED device with the dial actuator in a more open position, not obstructing as much of the exhalation aperture and perhaps not blocking any of the exhalation apertures in a fully open position. However, if the user goes to sleep with the dial actuator in the fully open position and proceeds to snore and disturb the bedtime partner, the bedtime partner can simply turn the dial actuator for the bedtime partner to help silence the snoring or could wake the partner and have them simply turn the dial actuator themselves to increase the strength without ever having to get out of bed or without needing to replace the device for another with more EPAP strength. Thus, the dial assembly has significant implications in tailoring therapeutic efficacy, especially in the context of optimizing exhalation resistance dynamically throughout the night as may be needed to achieve optimal therapeutic outcomes.

In other alternative embodiments sensors could be embedded within the NED device and used to monitor and report on airflow and sleep disordered breathing markers, such as airflow, respiratory rate, heart rate, oxygen saturation, possibly including wireless connection to the NED device to monitor and measure the efficacy of the NED device dial positions. Using this data, a NED device having a dial assembly according to the invention described herein could also incorporate an electronic, mechanical, spring, or other connection to automatically rotate the dial to a position based on the data readings and achieve continual optimal therapeutic levels without any user intervention. This automatic adjusting can take place throughout the night, moment to moment, as the optimal EPAP pressure tends to change throughout the night and in various parts of the sleep cycle. For example, OSA tends to get worse during REM sleep. In this example situation, a user may go to sleep, and early in the night when they are not in REM sleep the data feedback could indicate mild OSA and auto-position the dial to obstruct less of the exhalation apertures. However, when the user goes into REM sleep and the OSA becomes more severe, the data capturing this can signal to auto-position the dial to a stronger EPAP position where the dial obstructs more of the exhalation aperture. This is akin to how auto PAP change PAP based on the user's variable needs throughout the night.

The NED embodiments having a dial assembly could also have important implications in sleep testing and determining optimal therapeutic levels. For example, in sleep labs, the technicians often need to titrate PAP strength, ideally without waking the patient to determine optimal therapeutic positions. For example, in a sleep lab setting, the lab technician often starts a user on CPAP with a low pressure and then increases the pressure based on the data provided via the sleep test. This similar concept could be applied to a NED device where a technician would start a patient off with unobstructed exhalation apertures, thus having the least amount of EPAP resistance, which could be ideal for more mild forms of SDB or those persons who find more comfort with less backpressure. But if the patient requires more EPAP for therapeutic levels, the lab technician could simply rotate the dial actuator while the patient sleeps, have an auto-adjusting mechanism turn the dial actuator, or could wake the patient to have them adjust it themselves in order to find the optimal dial position and corresponding EPAP pressure. Or, similar to an auto PAP that self-adjusts to optimal pressures as described above, the patient could achieve optimal positioning without ever needing to go to a sleep testing center.

The embodiments were chosen and described to best explain the principles of the invention and its practical application to persons who are skilled in the art. As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting.

For example, the materials that are used to make the housings or the foam cover could be infused with a scent that can aid in breathing. It will also be appreciated that custom sizing via scans and 3D printed devices is possible, and embedded sensors can be used to monitor and report on airflow and sleep disordered breathing markers, such as airflow, respiratory rate, heart rate, oxygen saturation, possibly including wireless connection to devices to monitor and measure the efficacy of the NED device. Thus, the breadth and scope of the present invention should not be limited by any of the above-described exemplary embodiments, but should be defined only in accordance with the following claims appended hereto and their equivalents.

What is claimed is:

1. A nasal dilator for a nasal passageway that has a constriction therein in a baseline uninflamed state of a nasal vestibule, the nasal dilator comprising:

a first housing comprising a tubular sidewall with an interior surface, an exterior surface, an inner end, and an outer end, wherein the interior surface surrounds an interior space and extends between the inner end and the outer end, wherein the exterior surface is configured to be positioned within the nasal passageway, wherein an insertion of the first housing into the nasal passageway expands the nasal passageway from the baseline uninflamed state without the first housing inserted in the nasal passageway to a dilated state with the first housing inserted in the nasal passageway, and wherein the tubular sidewall produces a dilation of the nasal passageway in the dilated state with the interior space of the first housing being greater than the constriction of the nasal passageway in the baseline uninflamed state;

a first dial assembly comprising a dial actuator and a fitting sandwiched between the outer end of the first housing and the dial actuator, wherein the fitting comprises an inhalation port aligned with the interior space of the first housing and an exhalation aperture proximate to a perimeter of the inhalation port, wherein the dial actuator rotably connects to the fitting opposite from the first housing and comprises an aperture coaxially aligned with the inhalation port and the interior space, wherein the dial actuator rotates around a center axis of the aperture between a first position and a second position, and wherein the exhalation aperture has an unobstructed configuration in the first position and at least a partially obstructed configuration in the second position; and a first valve comprising a fixed end connected to at least one of the outer end of the first housing and the first dial assembly and a free end coaxially aligned with the aperture, the inhalation port and the interior space, wherein the first valve has an open configuration when an inhalation airflow passes from the outer end towards the inner end and a closed configuration when an exhalation airflow passes from the inner end towards the outer end, wherein the free end of the first valve does not block the exhalation aperture in either the closed configuration and the open configuration, wherein the first valve is configured to restrict the exhalation airflow in the closed configuration, and wherein the dilation in the nasal passageway and the open configuration of the first valve allow the inhalation airflow to pass more freely through the inhalation port and aperture of the first dial assembly and the interior space of the first housing in the dilated state than an unaided inhalation airflow which passes through the nasal passageway in the baseline uninflamed state without the first housing, the first dial assembly and the first valve.

2. The nasal dilator of claim 1, further comprising an open section situated within at least one of the dial actuator and the tubular sidewall, wherein the open section in the dial actuator is spaced a distance from the aperture, wherein the open section in the tubular sidewall is situated at a location proximate to the outer end, wherein the open section is positioned around the exhalation aperture in the first position, and wherein at least a portion of the exhalation aperture is removed from the open section in the second position.

3. The nasal dilator of claim 2, wherein the first housing further comprises a circumferential section comprised of the open section in the tubular sidewall and a circumferential groove within the interior surface proximate to the outer end, wherein the open section in the tubular sidewall is comprised of a slot, wherein the fitting further comprises a tubular body received within a section of the interior space of the housing proximate to the outer end, wherein the tubular body comprises a body sidewall with an interior side, an exterior side, an inner edge, an outer edge, and a circumferential flange, wherein the body sidewall surrounds the inhalation port extending between the inner edge and the outer edge, wherein the circumferential flange protrudes a flange length from the exterior side at a first location spaced a distance from the outer edge and seats against the outer end of the first housing, wherein the body sidewall further comprises a circumferential tongue protruding from the exterior side at a second location between the circumferential flange and the inner edge, wherein the circumferential tongue is received within the circumferential groove, and wherein at least a portion of the exhalation aperture is situated within body sidewall proximate to the second location.

4. The nasal dilator of claim 3, wherein the dial actuator rotates the tubular body of the fitting around the center axis between the first position and the second position, wherein the circumferential tongue rotates within the groove, wherein the slot is positioned around the exhalation aperture in the first position, and wherein at least a portion of the exhalation aperture is rotated away from the slot and at least a portion of the circumferential tongue is rotated into the slot in the second position.

5. The nasal dilator of claim 2, wherein the fitting further comprises a planar cover connected to the first housing proximate to the outer end, wherein the outer periphery of the free end further comprises an exhalation port, wherein the interior surface of the outer end of the housing further comprises an exhalation recess in fluid communication with the interior space of the first housing through the exhalation recess and the exhalation port, wherein the exhalation aperture is situated between the perimeter of the inhalation port and an edge region of the planar cover and is in fluid communication with the exhalation port, wherein a plan area of the inhalation port and the exhalation aperture is circumscribed by a periphery of the interior surface of the first housing, wherein the planar cover further comprises a plurality of side ends extending beyond the periphery, wherein the outer periphery of the free end of the valve extends beyond the inhalation port to the edge region of the planar cover and is circumscribed by the periphery, wherein the dial actuator further comprises a dial flange surrounding the aperture, wherein the open section is situated within the dial flange and is positioned around the exhalation aperture in the first position, and wherein the dial flange is positioned over at least a portion of the exhalation aperture in the second position.

6. The nasal dilator of claim 1, wherein the exterior surface of the first housing further comprises a protrusion proximate to at least one of the inner end and the outer end, wherein the first housing further comprises a first flange surrounding the tubular sidewall proximate to the outer end, wherein the first flange has an inward facing surface and an outward facing surface, wherein the inward facing surface is adjacent to an exterior periphery of the nasal vestibule, wherein the protrusion engages with an interior side of the nasal vestibule when the first housing is inserted in the nasal passageway, and wherein the first flange remains outside the nasal vestibule when the first housing is inserted in the nasal passageway.

7. The nasal dilator of claim 6, further comprising a second housing, a second dial assembly, and a second valve, wherein the second housing further comprises a second flange, wherein the first flange and the second flange are connected through a bridge section, and wherein the bridge section connecting the first flange and the second flange has a width greater than a diameter of the tubular sidewall of the first housing and the second housing.

8. The nasal dilator of claim 1, wherein the dial actuator rotates around the center axis into a third position, and wherein the exhalation aperture is in a fully obstructed configuration in the third position.

9. The nasal dilator of claim 1, wherein the fitting further comprises a plurality of exhalation apertures proximate to the perimeter of the inhalation port, wherein at least one of the exhalation apertures is in the unobstructed configuration in the first position, and wherein each of the exhalation apertures are in at least the partially obstructed configuration in the second position.

10. The nasal dilator of claim 1, further comprising a valve support adjacent to the valve opposite from the outer end of the first housing, wherein the valve support comprises a porous structure covering the inhalation port and the interior space that does not restrict the exhalation airflow and the inhalation airflow, and wherein the valve support prevents the free end of the valve in the closed configuration from extending through the inhalation port when the exhalation airflow passes from the inner end towards the outer end.

11. The nasal dilator of claim 1, wherein the dial actuator and the fitting each further comprise an inner surface and an outer surface, wherein the inner surface of the dial actuator faces the outer surface of the fitting, wherein the inner surface of the fitting is situated proximate to the outer end of the first housing, and wherein the outer surface of the dial actuator further comprises a peripheral grip surrounding the aperture.

12. A nasal dilator for a nasal passageway that has a constriction therein in a baseline uninflamed state of a nasal vestibule, the nasal dilator comprising:

a first housing comprising a tubular sidewall with an interior surface, an exterior surface, an inner end, and an outer end, wherein the interior surface surrounds an interior space and extends between the inner end and the outer end, wherein the tubular sidewall further comprises a circumferential section having a slot proximate to the outer end, wherein the exterior surface is configured to be positioned within the nasal passageway, wherein an insertion of the first housing into the nasal passageway expands the nasal passageway from the baseline uninflamed state without the first housing inserted in the nasal passageway to a dilated state with the first housing inserted in the nasal passageway, and wherein the tubular sidewall produces a dilation of the nasal passageway in the dilated state with the interior space of the first housing being greater than the constriction of the nasal passageway in the baseline uninflamed state;

a first dial assembly comprising a dial actuator and a fitting sandwiched between the outer end of the first housing and the dial actuator, wherein the fitting comprises a tubular body partially received within a section of the interior space of the housing proximate to the outer end, an inhalation port and an exhalation aperture, wherein the tubular body further comprises a body sidewall surrounding the inhalation port extending between a pair of opposing body ends, wherein the exhalation aperture is proximate to a perimeter of the inhalation port within the body sidewall, wherein the dial actuator rotably connects to a body end from the pair of body ends situated outside of the interior space and comprises an aperture coaxially aligned with the inhalation port and the interior space, wherein the dial actuator rotates the fitting around a center axis of the aperture between a first position and a second position, wherein the exhalation aperture has an unobstructed configuration with the exhalation aperture rotated into alignment with the slot in the first position, and wherein the exhalation aperture has at least a partially obstructed configuration with at least a portion of the exhalation aperture rotated out of alignment with the slot in the second position; and a first valve comprising a fixed end situated between the dial actuator and the fitting and a free end coaxially aligned with the aperture, the inhalation port and the interior space, wherein the first valve has an open configuration when an inhalation airflow passes from the outer end towards the inner end and a closed configuration when an exhalation airflow passes from the inner end towards the outer end, wherein the free end of the first valve does not block the exhalation aperture in either the closed configuration and the open configuration, wherein the first valve is configured to restrict the exhalation airflow in the closed configuration, and wherein the dilation in the nasal passageway and the open configuration of the first valve allow the inhalation airflow to pass more freely through the inhalation port and aperture of the first dial assembly and the interior space of the first housing in the dilated state than an unaided inhalation airflow which passes through the nasal passageway in the baseline uninflamed state without the first housing, the first body and the first valve.

13. The nasal dilator of claim 12, wherein the circumferential section of the first housing further comprises a circumferential groove within the interior surface, wherein the body sidewall further comprises an interior side, an exterior side, an inner edge, an outer edge, a circumferential flange, a circumferential tongue and a prong, wherein the circumferential flange protrudes a flange length from the exterior side at a first location spaced a distance from the outer edge and seats against the outer end of the first housing, wherein the circumferential tongue protrudes a tongue length from the exterior side at a second location between the circumferential flange and the inner edge, wherein the prong protrudes a prong length from the interior side at a third location between the inner edge and the outer edge, wherein the circumferential tongue is received within the circumferential groove and rotates therein, wherein the slot is positioned around the exhalation aperture in the first position, and wherein at least a portion of the exhalation aperture is rotated away from the slot and at least a portion of the circumferential tongue is rotated into the slot in the second position.

14. The nasal dilator of claim 12, further comprising a plurality of exhalation apertures within the body sidewall, wherein each of the exhalation apertures are circumferentially spaced from one another by a plurality of lands, wherein each of the exhalation apertures comprise an arc length, and wherein at least a pair of the arc lengths from the plurality of exhalation apertures are unequal.

15. The nasal dilator of claim 12, wherein the dial assembly further comprises a valve support sandwiched between the valve and the dial actuator, wherein the valve support comprises a porous structure covering the inhalation port and the interior space that does not restrict the exhalation airflow and the inhalation airflow, and wherein the valve support prevents the free end of the valve in the closed configuration from extending through the inhalation port when the exhalation airflow passes from the inner end towards the outer end.

16. The nasal dilator of claim 12, further comprising a second housing, a second dial assembly, and a second valve, wherein the first housing and the second housing are connected through a bridge section, and wherein the bridge section connecting the first housing and the second housing has a width greater than a diameter of the tubular sidewall of the first housing and the second housing.

17. A nasal dilator for a nasal passageway that has a constriction therein in a baseline uninflamed state of a nasal vestibule, the nasal dilator comprising:

a housing comprising a tubular sidewall with an interior surface, an exterior surface, an inner end, and an outer end, wherein the interior surface surrounds an interior space and extends between the inner end and the outer end, wherein the tubular sidewall further comprises a circumferential section having a slot and a circumferential groove within the interior surface proximate to the outer end, wherein the exterior surface is configured to be positioned within the nasal passageway, wherein an insertion of the housing into the nasal passageway expands the nasal passageway from the baseline uninflamed state without the housing inserted in the nasal passageway to a dilated state with the housing inserted in the nasal passageway, and wherein the tubular sidewall produces a dilation of the nasal passageway in the dilated state with the interior space of the housing being greater than the constriction of the nasal passageway in the baseline uninflamed state;

a dial assembly comprising a dial actuator and a fitting sandwiched between the outer end of the housing and the dial actuator, wherein the fitting comprises a tubular body partially received within a section of the interior space of the housing proximate to the outer end, an inhalation port and an exhalation aperture, wherein the tubular body comprises a body sidewall, an interior side, an exterior side, an inner edge, an outer edge, a circumferential tongue and a circumferential flange, wherein the body sidewall surrounds the inhalation port extending between the inner edge and the outer edge, wherein the exhalation aperture is proximate to a perimeter of the inhalation port within the body sidewall, wherein the dial actuator rotably connects to outer edge of the body sidewall and comprises an aperture coaxially aligned with the inhalation port and the interior space, wherein the dial actuator rotates the fitting around a center axis of the aperture between a first position and a second position, wherein the exhalation aperture has an unobstructed configuration in the first position and at least a partially obstructed configuration in the second position, wherein the circumferential flange protrudes a flange length from the exterior side at a first location spaced a distance from the outer edge and seats against the outer end of the first housing, wherein the circumferential tongue protrudes a tongue length from the exterior side at a second location between the circumferential flange and the inner edge and it is received within the circumferential groove, wherein the exhalation aperture has an unobstructed configuration with the exhalation aperture rotated into alignment with the slot in the first position, and wherein the exhalation aperture has at least a partially obstructed configuration with at least a portion of the exhalation aperture rotated out of alignment with the slot and at least a portion of the circumferential tongue rotated into the slot in the second position; and a valve comprising a fixed end situated between the dial actuator and the fitting and a free end coaxially aligned with the aperture, the inhalation port and the interior space, wherein the valve has an open configuration when an inhalation airflow passes from the outer end towards the inner end and a closed configuration when an exhalation airflow passes from the inner end towards the outer end, wherein the free end of the valve does not block the exhalation aperture in either the closed configuration and the open configuration, wherein the valve is configured to restrict the exhalation airflow in the closed configuration, and wherein the dilation in the nasal passageway and the open configuration of the valve allow the inhalation airflow to pass more freely through the inhalation port and aperture of the dial assembly and the interior space of the housing in the dilated state than an unaided inhalation airflow which passes through the nasal passageway in the baseline uninflamed state without the housing, the body and the valve.

18. The nasal dilator of claim 17, further comprising a plurality of exhalation apertures within the body sidewall, wherein each of the exhalation apertures are circumferentially spaced from one another by a plurality of lands, wherein each of the exhalation apertures comprise an arc length, and wherein at least a pair of the arc lengths from the plurality of exhalation apertures are unequal.

19. The nasal dilator of claim 17, wherein the fitting further comprises a prong protruding a prong length from the interior side at a third location between the inner edge and the outer edge, and wherein the free end of the valve contacts the prong in the open configuration.

20. The nasal dilator of claim 17, wherein the exterior surface of the housing further comprises a protrusion proximate to at least one of the inner end and the outer end, wherein the housing further comprises an outer flange surrounding the tubular sidewall proximate to the outer end, wherein the outer flange has an inward facing surface and an outward facing surface, wherein the inward facing surface is adjacent to an exterior periphery of the nasal vestibule, wherein the circumferential tongue seats against the outward facing surface of the outer flange, wherein the protrusion engages with an interior side of the nasal vestibule when the housing is inserted in the nasal passageway, and wherein the outer flange remains outside the nasal vestibule when the housing is inserted in the nasal passageway.

* * * * *